United States Patent
Ip et al.

(10) Patent No.: US 7,605,265 B2
(45) Date of Patent: Oct. 20, 2009

(54) HETERODIMERS AND METHODS OF USING THEM

(75) Inventors: Nancy Y Ip, Hong Kong (CN); Fanny Chui Fun Ip, Hong Kong (CN); Yueqing Hu, Hong Kong (CN); Yifan Han, Hong Kong (CN); Sookja Kim Chung, Hong Kong (CN)

(73) Assignee: Biotechnology Research Corporation Ltd., Hong Kong (CN)

( * ) Notice: Subject to any disclaimer, the term of this patent is extended or adjusted under 35 U.S.C. 154(b) by 0 days.

(21) Appl. No.: 11/625,603

(22) Filed: Jan. 22, 2007

(65) Prior Publication Data

US 2008/0176308 A1     Jul. 24, 2008

(51) Int. Cl.
C07D 219/12 (2006.01)
C07D 217/22 (2006.01)

(52) U.S. Cl. ........................... 546/106; 546/141

(58) Field of Classification Search .............. 546/106, 546/141
See application file for complete search history.

(56) References Cited

FOREIGN PATENT DOCUMENTS

WO    WO2006/127748 A1    11/2006

OTHER PUBLICATIONS

Carlier et al.Bioorganic and Medicinal chemistry Letters, 9(16), 2335-2338, 1999.*
International Search Report from PCT/US2008/051717 dated May 28, 2008, mailed Jun. 2, 2008.
Carlier, P.R. et al: "Potent, Easily Synthesized Huperzine A-Tacrine Hybrid Acetylcholinesterase Inhibitors," Bioorganic & Medicinal Chemistry Letters, Oxford, GB, vol. 9, No. 16, Aug. 16, 1999, pp. 2335-2338, XP004174186, ISSN: 0960-894X.
Written Opinion of the International Searching Authority.

* cited by examiner

*Primary Examiner*—D. Margaret Seaman
*Assistant Examiner*—Nizal S Chandrakumar
(74) *Attorney, Agent, or Firm*—Heslin Rothenberg Farley & Mesiti P.C.

(57) ABSTRACT

Novel heterodimers of tetrahydroacridines and tetrahydroquinolinones are disclosed. The heterodimers are capable of acting as both acetylcholinesterase inhibitors and N-methyl-D-aspartate (NMDA) receptor antagonists. The heterodimers may be used to improve cognitive defects via treatment or prevention in both humans and non-humans.

4 Claims, 9 Drawing Sheets

$* = P < 0.05$

HETERODIMERS AND METHODS OF USING THEM

FIELD OF THE INVENTION

The present invention broadly relates to novel heterodimers of tetrahydroacridines and tetrahydroquinolinones and their uses. In particular, the invention describes heterodimers which are capable of acting as both acetylcholinesterase inhibitors and N-methyl-D-aspartate (NMDA) receptor antagonists. The heterodimers may be used in the improvement of cognitive defects in both humans and non-humans. Such improvement can be in the form of both treatment and prevention of cognitive defects.

BACKGROUND

Within the central and peripheral nervous systems, neurons conduct nerve impulses by releasing neurotransmitters, chemicals that enable nerve cells to communicate. Acetylcholine (ACh) is a neurotransmitter which transmits nerve impulses in cholinergic neurons. ACh plays a crucial role in learning and memory. Decreased presence of acetylcholine has been found in Parkinson's disease (PD), dementia due to multiple strokes, multiple sclerosis, schizophrenia, and is a major characteristic of Alzheimer's disease (AD). In addition, autopsy studies on patients with AD have revealed lesions in the cholinergic neurons of the nucleus basalis. Thus, the loss of ACh is thought to account for the loss of cognitive functions such as learning and memory that is a characteristic of many forms of dementia, including Alzheimer's disease-related dementia.

N-methyl-D-aspartate (NMDA) receptors are ligand-gated ion channels located primarily within the central nervous system (CNS). They belong to the family of ionotropic glutamate receptors and exist as multiple subtypes due to the different combinations of subunits—NR1, NR2 (NR2A, NR2B, NR2C, NR2D) and NR3—that can be expressed. They exhibit multiple distinct binding sites. Therefore, in addition to the agonist binding site, there are binding sites for various compounds that enhance, modulate and inhibit the activation of the receptor.

NMDA receptors are involved in neuronal communication and play important roles in synaptic plasticity and mechanisms that underlie learning and memory. Under normal conditions, the NMDA receptors engage in synaptic transmission via the neurotransmitter, glutamate. However, abnormally high levels of glutamate (due to a diseased state) lead to over-activation of these receptors resulting in an excess of $Ca^{2+}$ influx. This results in neuronal damage through the generation of free radicals such as nitric oxide (NO) and reactive oxygen species (ROS), loss of ATP, and loss of mitochondrial membrane potential. Decreased nerve cell function and neuronal cell death eventually occur. Known as excitotoxicity, this process also occurs if the cell's energy metabolism is compromised.

NMDA over-activation is implicated in neurodegenerative diseases and other pathological conditions as it causes neuronal loss and cognitive impairment. In fact, NMDA receptor-mediated excitotoxicity plays a part in the final common pathway leading to neuronal injury in a variety of neurodegenerative disorders such as Parkinson's disease, Alzheimer's disease and Huntington's disease, as well as conditions such as stroke and neuropathic pain. In fact, recent findings have implicated NMDA receptors in many more neurological disorders than previously thought such as multiple sclerosis, cerebral palsy (periventricular leukomalacia), and spinal cord injury, as well as in chronic and severe mood disorders (Mathew et al., 2005)

Compounds currently known in the art exhibit either cholinergic activity or NMDA antagonist activity—but not both. A number of tacrine derivatives (bis-tacrines, chloro-substituted bis-tacrines, chloro-substituted tacrines, etc.) have also been developed to treat Alzheimer's disease. While these compounds are reported to be highly potent and selective against AChE, no NMDA antagonist activity has been detected.

Cholinergic compounds exhibiting acetylcholinesterase inhibitory activity are known and available in the market. Donepezil, galantamine and rivastigmine are recognized and readily prescribed cholinergic drugs that have received FDA approval for mild to moderate Alzheimer's disease. While these drugs show slightly different pharmacological properties, they all work by inhibiting the breakdown of acetylcholine. The major difference between these compounds and those of the present invention is that they exert their influence via a single mechanism of action only, i.e. the inhibition of acetylcholinesterase. They are not NMDA receptor antagonists. Thus, their therapeutic purpose is focused primarily on enhancing the cholinergic effect. Furthermore, these compounds are only suitable for early stage dementia in AD.

Due to recent findings of the involvement of NMDA receptors in a variety of neuropathic disease states and conditions, NMDA antagonists as therapeutic drugs have become more commonly researched. One obstacle to the development of NMDA antagonists as neurotherapeutic drugs is that despite their significant neurotherapeutic potential, many promising NMDA antagonists also exhibit psychotogenic and neurotoxic properties. For example, MK-801 (dizocilpine maleate) has been shown to confer a degree of neuroprotection in ischemic stroke. MK-801, however, is also associated with pyschotropic and adverse motor effects. A few NMDA antagonists have been approved for clinical use for a variety of neuro-pathological conditions such as epilepsy and neuropathic pain and neurodegenerative diseases such as Alzheimer's disease (AD) and Parkinson's disease (PD). Memantine is a non-competitive NMDA antagonist recently approved (in 2004) for the treatment of vascular dementia and dementia symptoms in moderate to severe cases of Alzheimer's disease. Memantine is the only compound in this class of compounds that has successfully received FDA-approval for AD. The mechanism of inhibiting glutamate-induced neurotoxicity is similar to that of the novel compounds. However, unlike the novel compounds, memantine does not affect the cholinergic synaptic pathway.

However, recently the known potent AChE inhibitor, bis-9-amino-1,2,3,4-tetrahydroacridine (also known as bis(7)-tacrine), has also been shown to interact with NMDA receptors to reduce glutamate-induced excitotoxicity, a mechanism independent of its AChE inhibitory and cholinergic transmission activities (Li et al, 2005).

Huperzine A, another known potent anti-cholinesterase inhibitor isolated from the Chinese club moss *Huperzia serrata*, also has the ability to interact with the NMDA receptor in a non-competitive manner (Gordon et al, 2001). Huperzine A can protect against excitotoxicity by blocking NMDA ion channels and unlike MK-801 and other NMDA antagonists, does so in the absence of psychomimetic side-effects. This makes Huperzine A an ideal candidate for treating acute and chronic neuro-related disorders. However, as Huperzine A is derived from a naturally occurring herb, it is not patentable and thereby has little chance of being developed into a therapeutic drug by biopharmaceutical companies.

It is an object of the present invention to provide improved or alternative compounds useful for the treatment or prevention of neurodegenerative disorders.

SUMMARY OF THE INVENTION

The invention broadly comprises a compound which comprises amino-tetrahydroquinolinone and tetrahydroacridine moieties.

More specifically the invention broadly comprises compounds of Formula I:

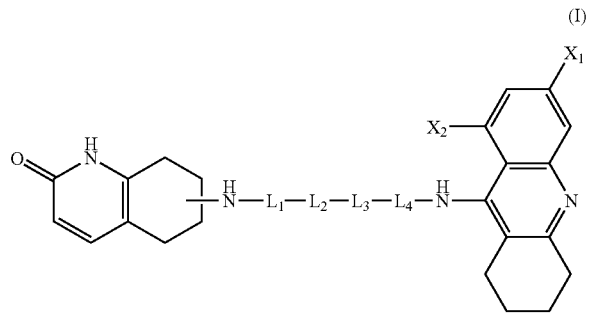

Wherein $X_1$, $X_2$ are independently selected from H, alkyl, halo, alkoxy;

L1, L2, L3, L4 are bonds independently selected from bivalent $C_{1-5}$ alkylene; 1,4-cyclohexylene, 1,4-phenylene, —CO—, —O—, —S— and —NR—;

R is selected from hydrogen, an unsubstituted or substituted alkyl, an unsubsituted or substituted cycloalkyl, unsubstituted or substituted alkenyl, or unsubstituted or substituted aryl;

with the proviso that when the tetrahydroquinolone is connected at 5-amino position, and L1-L2-L3-L4 is a $C_{3-12}$ methylene linker, then one of $X_1$ or $X_2$ is not H.

In a preferred embodiment, $X_1$ or $X_2$ is Cl.

In yet a further preferred embodiment the tetrahydroquinolinone moiety is connected at either the 5 or 6 positions.

The invention also comprises stereoisomers of compounds according to Formula 1.

In a further aspect the invention broadly comprises a method of inhibiting a cholinesterase comprising exposing the cholinesterase to a compound of Formula 1.

In a preferred embodiment the cholinesterase is selected from acetylcholinesterase or butyrylcholinesterase. In a particularly preferred embodiment the cholinesterase is in an animal and the compound of Formula 1 is administered to said animal. Preferably the cholinesterase to be inhibited is acetylcholinesterase or butyrylcholinesterase.

The invention also describes a method of inhibiting an N-methyl-D-aspartate receptor in an animal comprising administering to said animal an amount of a compound of Formula 1.

In a further aspect of the invention, there is described a method of inhibiting cholinesterase and N-methyl-D-aspartate receptors in an animal comprising administering to said animal an amount of a compound of Formula 1. Preferably the cholinesterase to be inhibited is acetylcholinesterase or butyrylcholinesterase.

In a further aspect the invention describes a method of treating a disease or disorder of the nervous system of an animal comprising administering an amount of a compound according to Formula 1. In a preferred embodiment the disease is a neurodegenerative disease. In a particularly preferred embodiment the neurodegenerative disease is Alzheimer's disease, Parkinson's disease or Huntington's disease.

In an alternative embodiment the disorder of the nervous system is caused by a stroke or epileptic fit.

In a further aspect the invention broadly describes a method of treating Alzheimer's disease, Parkinson's disease, Huntington's disease, or dementia in an animal comprising administering an amount of a compound according to Formula 1.

The invention also describes a method of preventing stroke, epilepsy or brain trauma in an animal comprising administering an amount of a compound according to Formula 1.

Also described by the invention is a method of improving cognitive ability in an animal comprising administering a compound according to Formula 1.

The methods of the invention are preferably carried out on mammals, more preferably humans.

In a further aspect the invention describes the use of a compound according to Formula 1 in the manufacture of a medicament useful for the treatment of dementia, Alzheimer's disease, Parkinson's disease or Huntington's disease; the prevention of stroke, epilepsy or brain trauma; and the improvement of cognitive ability.

DETAILED DESCRIPTION OF THE INVENTION

Figure 1:
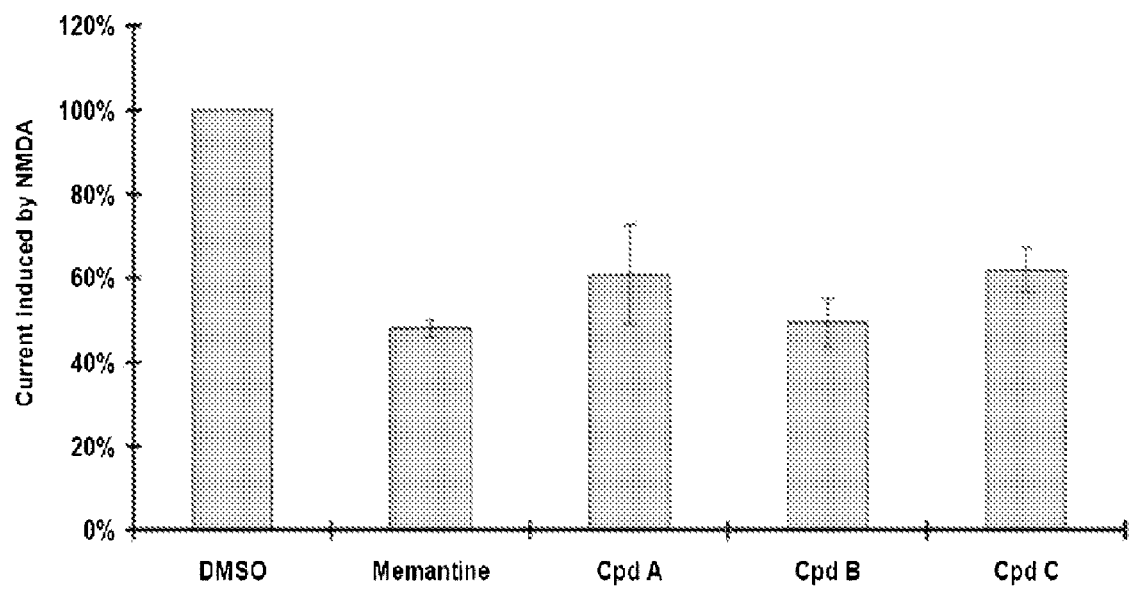
FIG. 1 is a graph comparing the NMDA receptor antagonist activity of compounds of the present invention with known NMDA antagonists.

To date, the most successful approach in reducing the rate of cognitive decline in AD patients has been based on blocking the enzyme acetylcholinesterase (AChE). AChE is responsible for breaking down ACh after it is released into the synaptic cleft as a result of nerve impulses. By temporarily blocking the activity of AChE via acetylcholinesterase inhibitors (AChEIs), the concentration of ACh in the bram and spinal cord is increased and its effects sustained. This mechanism of action (also known as the cholinergic effect) enhances the function of central cholinergic neurons which govern the process of learning and memory. In clinical evaluation, AChEIs have shown to improve cognition and memory in Alzheimer's patients. In fact, the FDA-approved drugs for first-line treatment of mild-moderate AD—donepezil, galantamine and rivastigmine—are reversible AChEIs. The memory and learning attributes of the compounds of the present invention have been demonstrated in animal models.

In addition to the classical role of AChE, recent reports have implicated AChE in a non-classical role of action in the brain. Although both AChE and BChE are found in the neuritic plaques of AD brains, only AChE has been found to promote the amyloid-beta (Aβ) fibrils assembly and accelerate the deposition of plaques (Inetrosa et al., 1996). In contrast, BChE attenuates amyloid fibril formation in vitro (Diamant et al., 2006). Inhibitors against the catalytic binding site of AChE increase the level of acetylcholine in brain while inhibitors to the peripheral anionic binding site (PAS) of the enzyme can prevent the pro-aggregating activity of AChE towards Aβ (Piazzi et al., 2003).

The novel compounds of Formula I also have the ability to confer neuroprotection. In particular, they are useful for protecting nerve cells and tissues subjected to glutamate-induced stress from damage by blocking the actions of the N-methyl-D-aspartate (NMDA) receptor (as opposed to simply treating damage thereof).

In light of the role of NMDA receptors in neuron-pathological conditions, NMDA receptor antagonists have been identified as therapeutic agents for excitotoxicity to alleviate symptoms of its associated neuronal disorders, conditions that currently have few, if any, effective treatments. Compounds of the present invention are therefore potential therapeutic agents for acute and chronic disorders of the central nervous system (CNS), such as neurodegenerative diseases, chronic pain, stroke and epilepsy.

By preventing efficient receptor activation and synapse transmission by glutamate, the compounds encompassing the invention can prevent excitotoxicity and its associated downstream events that lead to neuronal tissue injury and death, and diseased states.

The compounds of Formula I exhibit two modes of action. Like the cholinergic drugs, they inhibit acetylcholinesterase in neuronal synapses of cholinergic neurons to enhance the cholinergic effect, thus playing an important role in enhancing cognitive deficits in dementia and AD-related dementia. They also act as NMDA receptor antagonists and protect against glutamate-induced neurotoxicity which has been implicated in many neuropathic diseases and disorders.

The compounds of Formula I thus represent a new generation of compounds that both protect against glutamate-induced neurotoxicity as well as enhance cognitive deficits in diseased brains. They are novel in the sense that they encapsulate two key mechanisms of activity both of which play important roles in the progression of diseases such as AD. In fact, recent research suggests that AChE inhibitors that exhibit the ability to prevent glutamate-induced neuronal apoptosis may be of greater therapeutic value in the treatment of AD than pure AChE inhibitors (Li et al, 2005).

Furthermore, in clinical practice on the management of AD, studies are underway on determining the efficacy of combination treatments—administration of both an NMDA antagonist (memantine) and a cholinergic drug (donepezil, galantamine or rivastigmine). Therefore, compounds such as the invention may harbour greater therapeutic benefits than those found in existing AD drugs.

The compounds of Formula I also exhibit a strong selectivity towards AChE over BChE. This selectivity enables AChEI to inhibit AChE induced aggregation of Aβ. Tacrine, on the other hand, is a non-selective mixed-type AChE inhibitor which binds more tightly to BChE. Thus, tacrine has no effect on AChE-promoted Aβ aggregation. Another example is the PAS binding inhibitor, propidium, which is less selective towards BChE compared to AChE, and thus, strongly inhibits the AChE-promoted Aβ aggregation. Therefore, the selectivity of inhibitors to AChE then BChE is suggested to be an important factor when searching for novel potential therapeutic candidates (Bolognesi et al., 2005).

Schematic methods for producing the compounds of the invention are as follows.

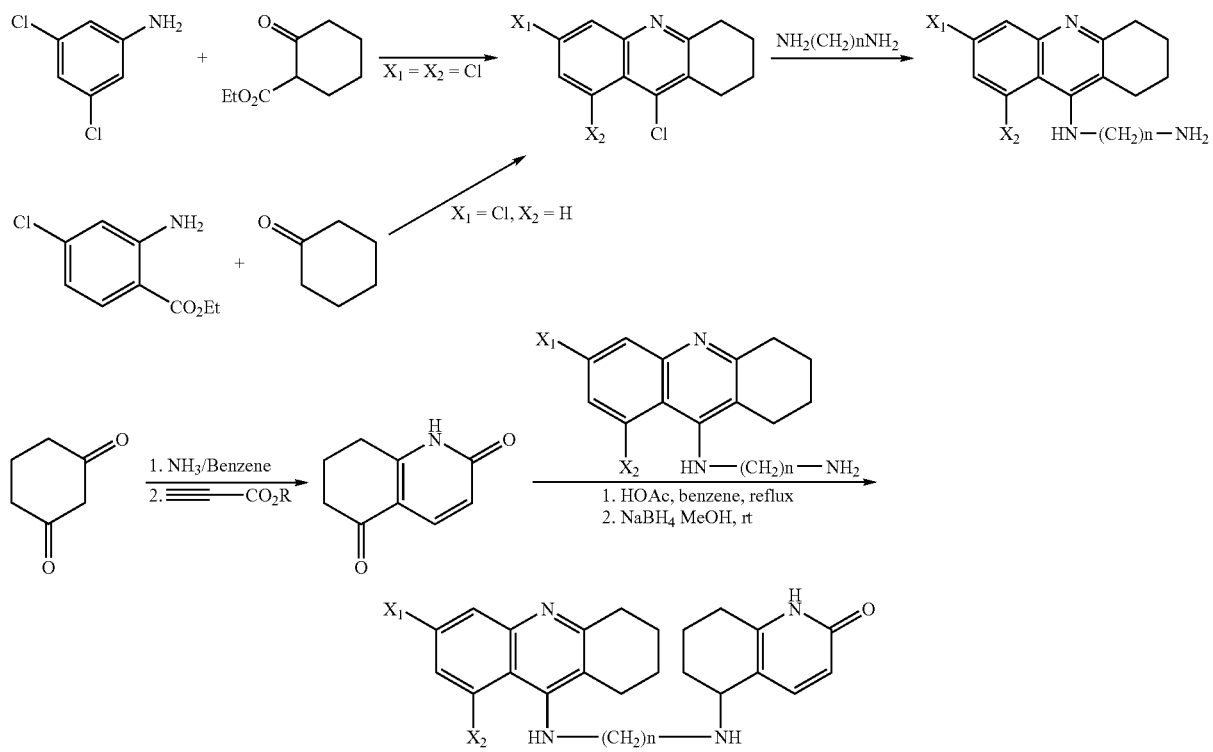

Scheme 1 Synthesis of racemic heterodimers

-continued
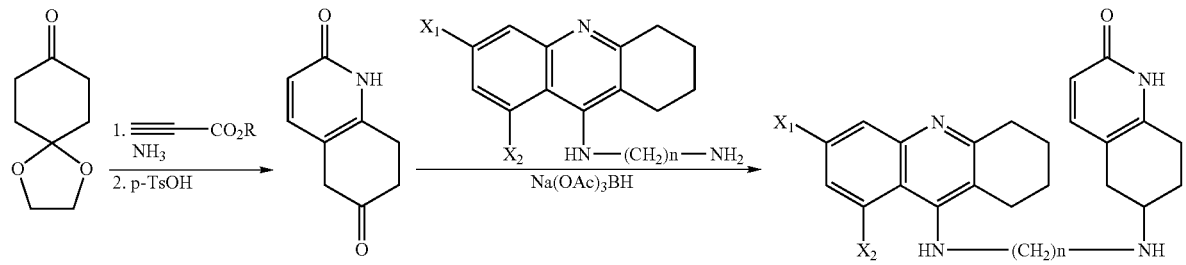
Scheme 2 Synthesis of enantiomerically pure heterodimers
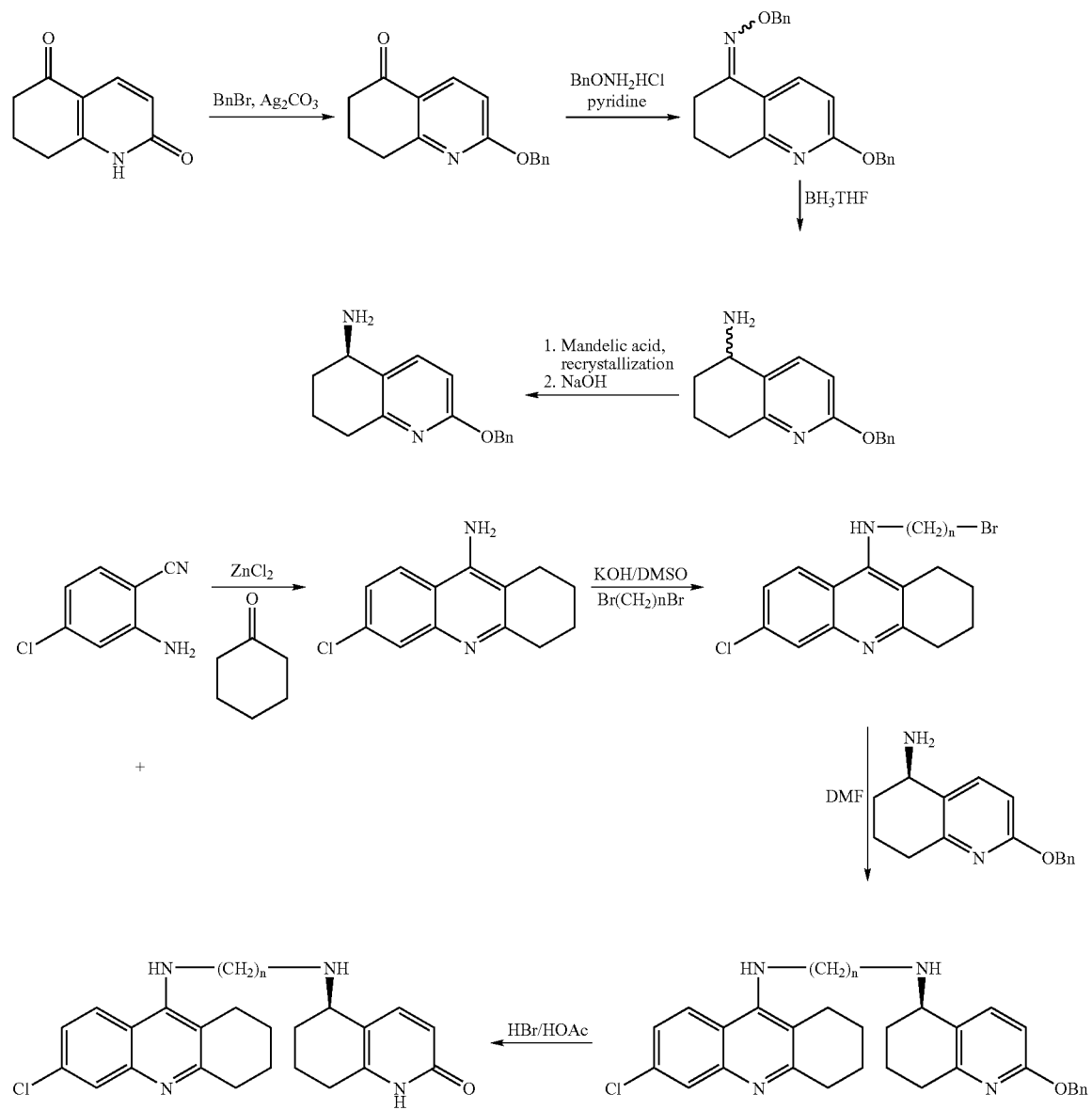

The invention will now be described with reference to a number of working examples. These are provided as a guide to the skilled reader to performing the invention, and are not intended to limit the scope of the claims in any way.

EXAMPLES

A number of compounds of the invention were subjected to experimental procedures to test their respective abilities to confer neuroprotection and to reverse or hinder neurological damage in animal subjects. The tested compounds had the following formulas:

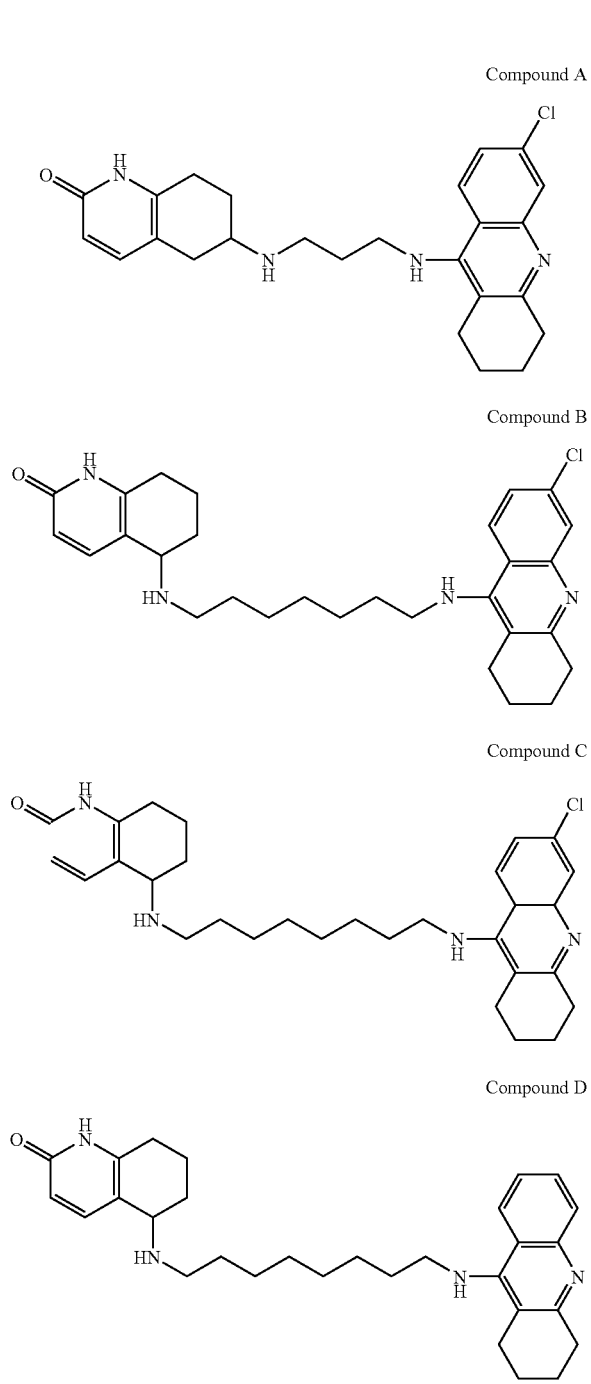

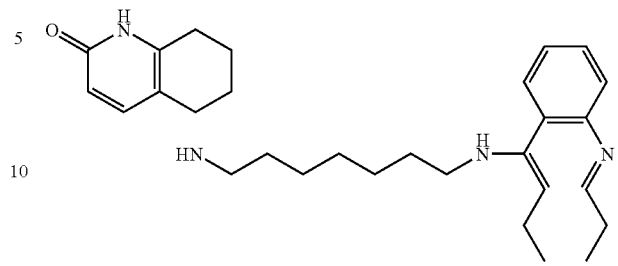

Example 1

In Vitro Inhibition of AChE and BChE

The in vitro inhibition of the enzymes acetylcholinesterase (AChE) and butyrylcholinesterase (BChE) were assessed. BChE, like AChE, breaks down acetylcholine (ACh) but is found in plasma and other organs such as the liver, skin and gastrointestinal tract. Since BChE inhibition may lead to unwanted side-effects, the compounds of Formula I were evaluated for: (i) potent inhibition of AChE and (ii) a strong selectivity for AChE over BChE.

The anti-acetylcholinesterase activity of the compounds was demonstrated by performing a cholinesterase assay and measuring enzyme inhibition using a spectrophotometric method based on the Ellman method. The enzymes, AChE and BChE, used in the inhibition studies were prepared from the cortex and serum of decapitated rats, respectively. The concentration required to yield 50% enzyme inhibition ($IC_{50}$) was determined for each of the novel compounds of Formula I. The results are presented in Table 1.

TABLE 1

AChE inhibitory activity of novel compounds of Formula 1

| Tested compound | AChE $IC_{50}$ (nM) | BChE $IC_{50}$ (nM) | Selectivity AchE* |
|---|---|---|---|
| Compound A | 0.2497 ± 0.05 | 56.74 ± 25 | 227.23 |
| Compound B | 0.0068 ± 0.003 | 31.09 ± 1.96 | 4563 |
| Compound C | 0.0127 ± 0.002 | 637.9 ± 121.6 | 50317.32 |
| Compound D | 13.64 ± 1.76 | 429.87 ± 46.72 | 31.52 |
| Compound E | 11.95 ± 1.66 | 610.11 ± 43.99 | 51.11 |
| Tacrine | 143.3 ± 32.5 | 44.43 ± 15.3 | 0.31 |
| bis(7)-tacrine | 13.2 ± 1.4 | 404 ± 21 | 30.6 |

*Selectivity for AChE is defined as $IC_{50}$ (BChE)/$IC_{50}$ (AChE)

Tacrine and bis(7)-tacrine, both known AChE inhibitors, were included for comparison. Bis(7)-tacrine is a potent and selective inhibitor of AChE but as the data in Table 1 indicates, compounds A, B and C exhibited higher potency and selectivity towards AChE than tacrine or bis(7)-tacrine. Compound A, B and C were ~200, 20471, and 11000 times more potent than tacrine, respectively, and ~53, 1885 and 1039 times more potent than bis(7)-tacrine.

Example 2

NMDA Receptor Antagonist Activity

Whole cell patch clamp studies were conducted to measure the ion current across the surface of hippocampal neurons in the presence and absence of the novel compounds to demonstrate NMDA receptor activity. The NMDA receptor is a gated ion channel, which allows inflow of current during a nerve impulse. Antagonists to the receptor would prevent the inflow of current. Memantine, a known NMDA antagonist was used as the positive control.

Hippocampal neurons from embryonic day 18 rats were isolated, trypsinized, plated onto 35-mm plates at a density of $3 \times 10^4$ cells/plate and cultured in Neurobasal medium (NB) supplemented with B27 nutrient. DIV10-14 rat hippocampal neurons were treated with NMDA (50 μM) in the absence or presence of the novel compounds (Cpd A, B and C) (10 μg/mL). Data is presented as % of NMDA-induced current. DMSO is the solvent control. FIG. 1 shows that compounds A, B, and C decreased NMDA-induced current in hippocampal neurons.

Example 3

Novel Compounds Protect Rat Cortical Neurons Against NMDA Excitotoxicity

The compounds were subjected to NMDA survival assays to investigate their ability to prevent NMDA receptor-induced excitotoxicity. The NMDA survival assay was performed to measure the degree of protection provided to cortical neuronal cells when treated with the compounds prior to an ischemic insult.

Figure 2:
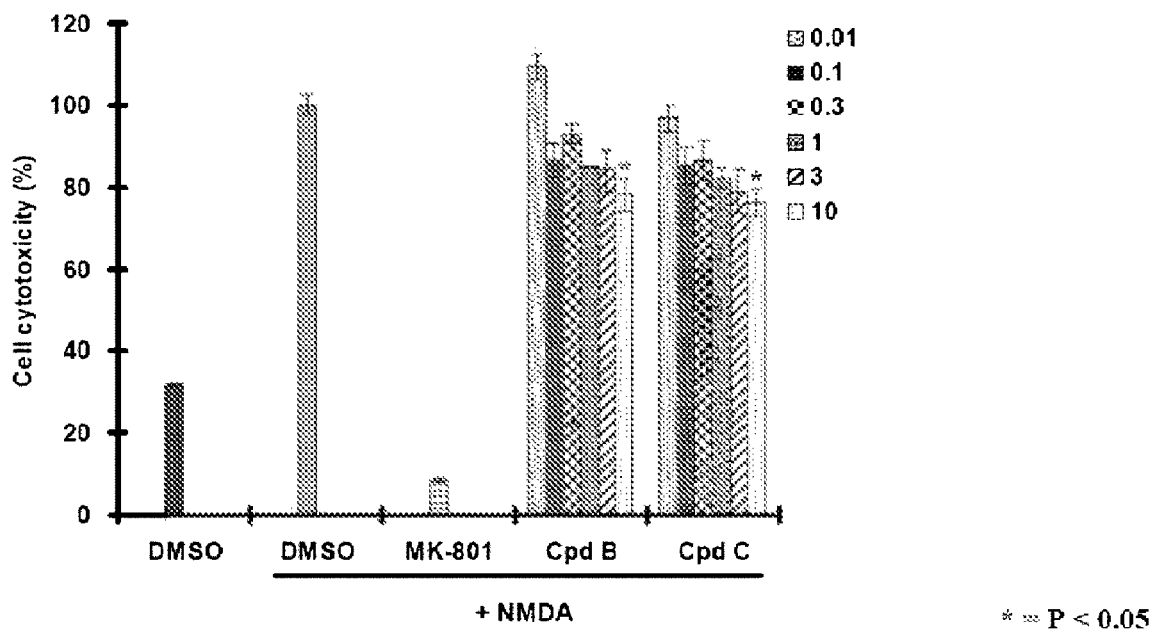
FIG. 2 is a graph showing the ability of the claimed compounds to protect rat cortical neurons against NMDA excitotoxicity.

DIV10 cortical neurons were treated with NMDA (20 μM) in the presence of compound (cpd) B or C (μg/mL). LDH release in the medium was detected at 24 hr after treatment. DMSO was used as the solvent control, while MK-801 (10 μM) is a known NMDA antagonist. FIG. 2 demonstrates that cpds B and C were able to protect rat cortical neurons against NMDA excitotoxicity.

Figure 3:
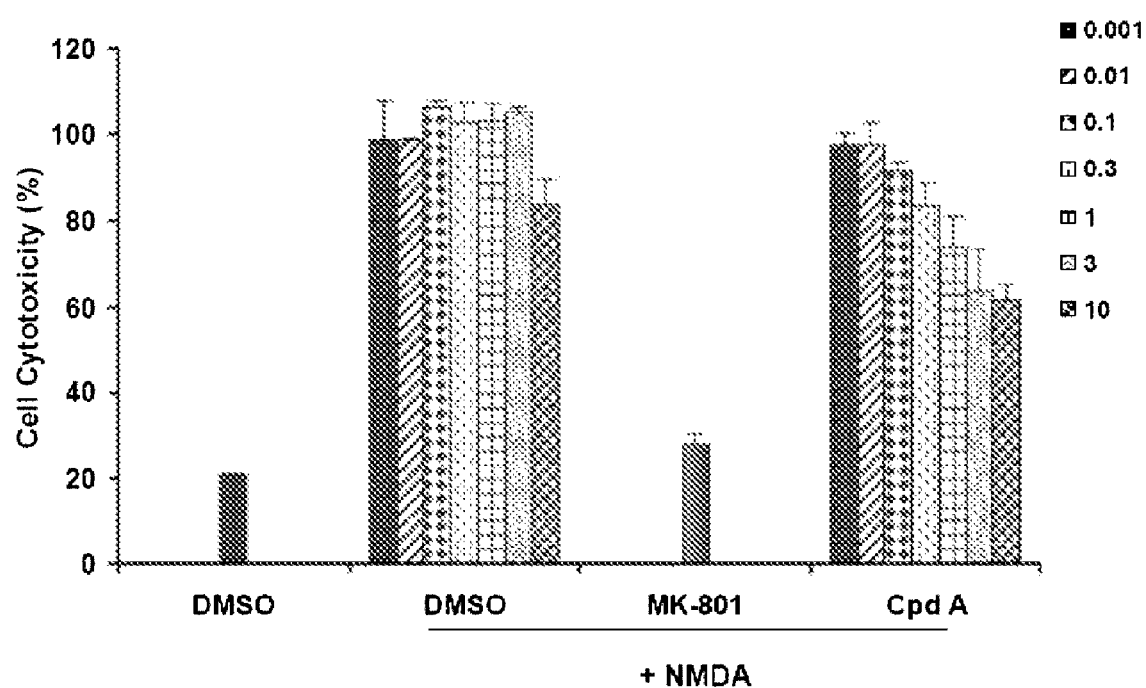
FIG. 3 is a graph showing the ability of a claimed compound to protect cortical neurons against NMDA insults (measured by cell death percentages).

DIV11 rat cortical neurons were treated with NMDA (20 μM) in the absence or presence of compounds (MK-801, 10 μM; compound A, 0.001-10 μg/mL). LDH release in the medium was detected at 24 hr after treatment. DMSO was used as the solvent control. FIG. 3 demonstrates that compound (cpd) A is capable of protecting cortical neurons against NMDA insults.

Example 4

Novel Compounds Enhance Learning and Memory in In Vivo Studies

The effect of the compounds on spatial learning and memory in young adult rats was demonstrated using a Morris water maze task, the favored test to study hippocampal-dependent learning and memory. The Morris water maze consists of a water pool with a hidden, submerged escape platform. The rats must learn, over a period of consecutive days, the location of the platform using either contextual or local cues. The time taken to locate the hidden platform (escape latency) is a measure of the animal's cognitive abilities.

For compound B (FIG. 4a), the test subjects in the control group (sham) took ~20 seconds to detect the platform after 4 days of training. In contrast, the scopolamine-induced memory-impaired group required more than twice the amount of time to locate the platform after an identical training period. Subsequent administration of compound B reversed the increased escape latency induced by scopolamine at a concentration of 0.1 mg/kg more efficiently than 1.5 mg/kg of tacrine (THA).

Figure 4A:
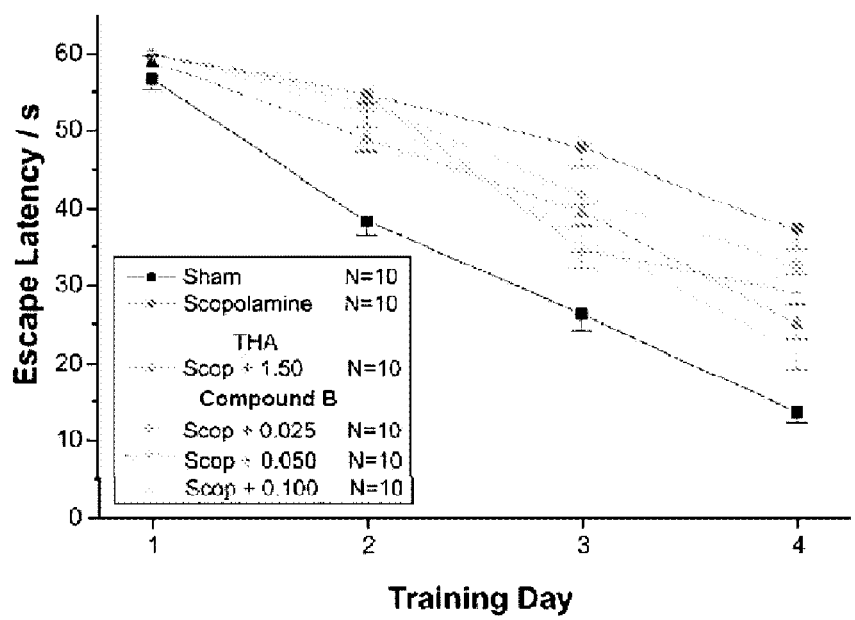
FIGS. 4a to 4f are graphs showing the ability of the claimed compounds to reverse scopolamine-induced performance deficits in Morris Water Maze tests.

Scopolamine (0.1 mg/kg) was first i.p. administered to young adult rats to impair their memories. Scopolamine-induced memory impaired rats were then orally administered one of three different doses of compound B (0.025, 0.050, or 0.100 mg/kg) and subjected to the Morris water maze over a period of 4 days. On each day, the time taken for the rats to detect the hidden platform in the water maze was measured, in seconds. For comparison purposes, tacrine (1.5 mg/kg) was similarly administered to scopolamine-induced memory impaired rats but was less effective in shortening escape latency. FIG. 4a demonstrates that compound B reverses scopolamine-induced performance deficits in the Morris Water Maze test.

For the compound designated C (FIG. 4b), the test subjects in the control group (sham) took less than 20 seconds to detect the platform after 4 days of training, while the scopolamine-induced memory-impaired group took ~40 seconds. Compound C significantly reversed the increased escape latency induced by scopolamine at the concentration of 0.4 mg/kg. Compound C at concentrations of 0.2 mg/kg and 0.4 mg/kg was more effective that 1.5 mg/kg tacrine (THA).

Figure 4B:
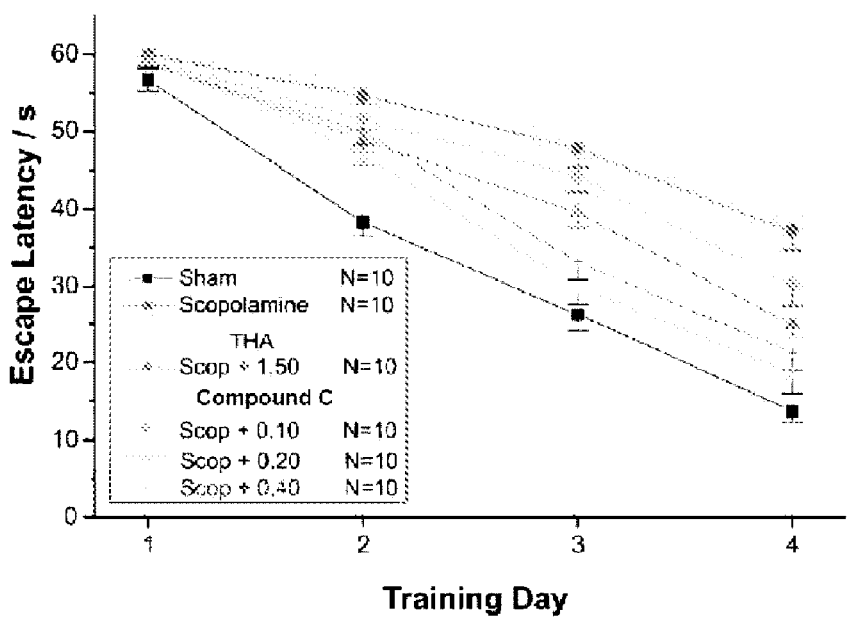

Scopolamine (0.1 mg/kg) was first i.p. administered to young adult rats to impair their memories. Scopolamine-induced memory impaired rats were then orally administered one of three different doses of compound C (0.1, 0.2, or 0.4 mg/kg) and subjected to the Morris water maze over a period of 4 days. On each day, the time taken for the rats to detect the hidden platform in the water maze was measured, in seconds. For comparison purposes, tacrine (1.5 mg/kg) was similarly administered to scopolamine-induced memory impaired rats but was less effective in shortening escape latency. FIG. 4b demonstrates that compound C reverses scopolamine-induced performance deficits in the Morris Water Maze test.

For compound A (FIG. 4c), the test subjects in the control group (sham) took less than 20 seconds to detect the platform after 4 days of training, while the scopolamine-induced memory-impaired group took ~50 seconds. Compound A significantly reversed scopolamine-induced performance deficits at concentrations of 0.2 and 0.4 mg/kg.

Figure 4C:
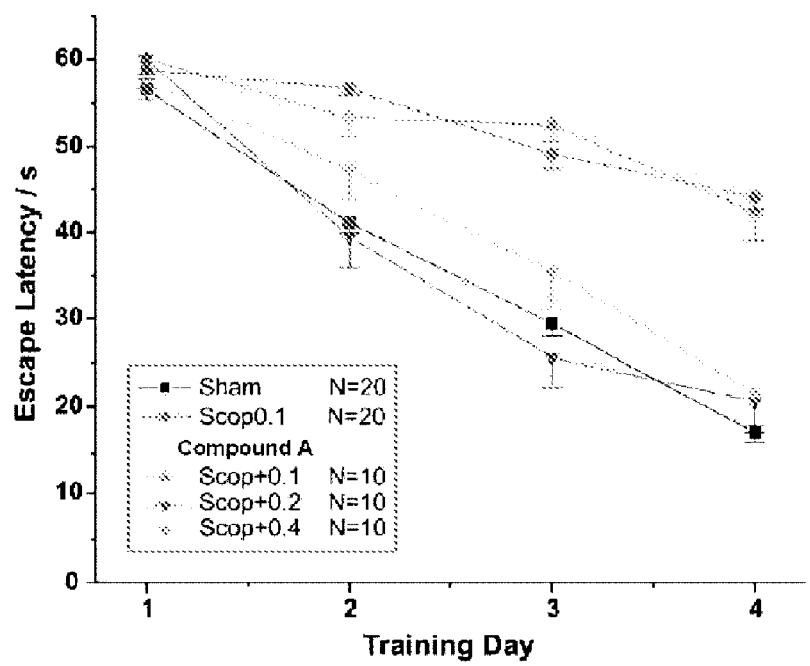

Scopolamine (0.1 mg/kg) was first i.p. administered to young adult rats to impair their memories. Scopolamine-induced memory impaired rats were then orally administered one of three different doses of compound A (0.1, 0.2, or 0.4 mg/kg) and subjected to the Morris water maze over a period of 4 days. On each day, the time taken for the rats to detect the hidden platform in the water maze was measured, in seconds. FIG. 4c demonstrates that compound A reversed scopolamine-induced performance deficits in the Morris Water Maze test.

A spatial bias (% of total distance swum in the training quadrant during spatial probe trial) for the region of the apparatus where the platform was positioned during training was also measured for compounds B and C. Scopolamine-induced memory impaired rats exhibited ~25% spatial bias in contrast to 40% observed in non memory-impaired control rats. Administration of compound B (FIG. 4d), C (FIG. 4e) or A (FIG. 4f) to memory-impaired rats, however, significantly increased spatial bias.

Figure 4D:
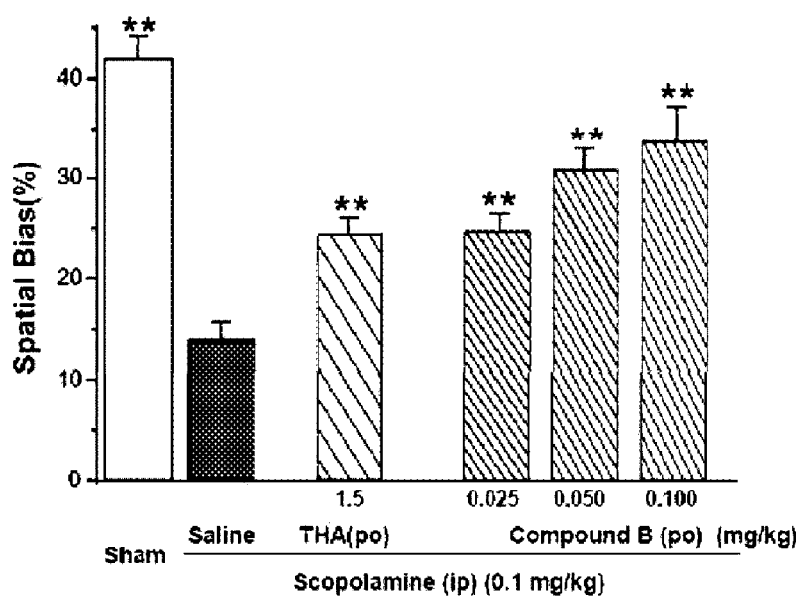

The spatial bias for the region of the testing apparatus where the hidden platform was positioned during training was measured. Administration of compound B resulted in increased spatial bias compared to the memory-impaired group with no drug administration (black bar). Compound B (0.05 and 0.1 mg/kg) exhibited spatial bias close to control levels (sham: non memory-impaired rats). Tacrine (THA) was included for comparison purposes. FIG. 4d shows the effect of oral administration (p.o.) of compound B on scopolamine (0.1 mg/kg)-treated mice on spatial bias (% of total distance swum in the training quadrant during spatial probe trial).

Figure 4E:
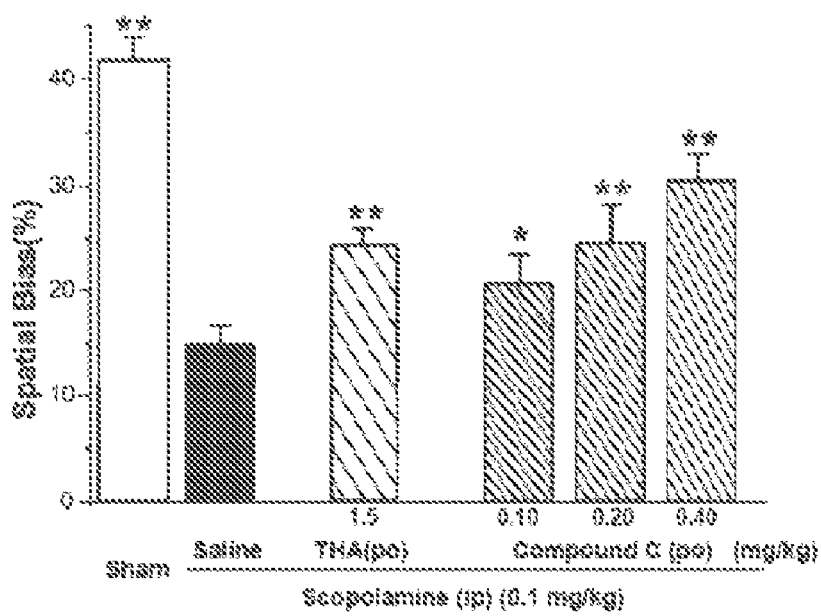

FIG. 4e shows the effect of compound C on scopolamine-induced (0.1 mg/kg) spatial bias (% of total distance swum in the training quadrant during spatial probe trial). Administration of compound C increased spatial bias compared to the memory-impaired group with no drug administration (black bar). Compound C at dosages of 0.2 and 0.4 mg/kg exhibited spatial bias close to control levels (sham: non memory-impaired rats). Tacrine (THA) was included for comparison purposes.

Figure 4F:
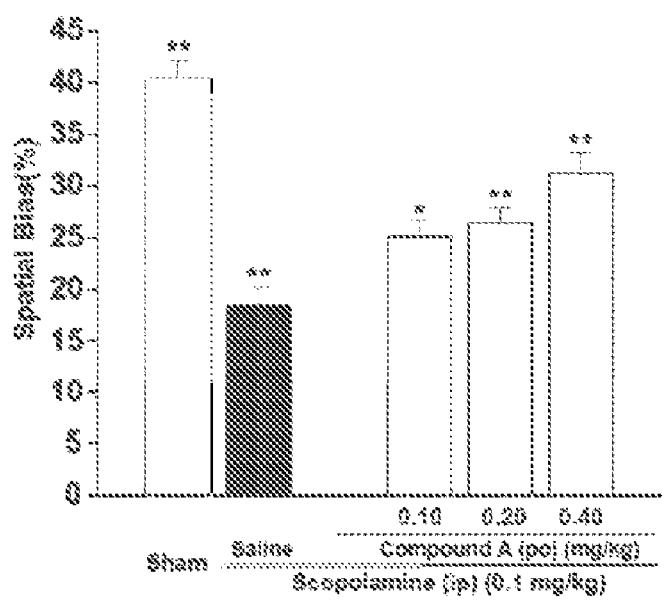

FIG. 4f shows the effect of compound A on scopolamine-induced (0.1 mg/kg) spatial bias (% of total distance swum in the training quadrant during spatial probe trial). Administration of compound A increased spatial bias compared to the memory-impaired group with no drug administration (black bar). Compound A at dosages of 0.2 and 0.4 mg/kg exhibited spatial bias close to control levels (sham: non memory-impaired rats).

Example 5

Investigation of Protective Effects Conferred on Test Subjects

The MCAO (middle carotid artery occlusion model) was performed to investigate the protective effects of compounds A, B and C on the brain when the brain was exposed to transient focal ischemia (lack of oxygen), emulating brain conditions during a stroke. Three main types of data were obtained from this investigation.

(i) Neurological deficits were observed in mice after 22 hours of reperfusion. The ability of the novel compounds to protect against the appearance of these neurological deficits was examined using a four-point scale neurological scoring system (Mann Whitney U test). For each of the following observable signs, the distribution of test subjects was noted (with and without treatment with the invention after ischemia): (0) no observable neurological deficits (normal); (1) failure to extend the left forepaw fully (mild); (2) circling to the contralateral side (moderate); and (3) loss of walking and righting reflex (severe).

(ii) The brains of the test subjects slices were sectioned into five pieces and the infarct area and volume of each slice was measured. The % of infarct area in test subjects treated with the invention after ischemia was compared to that of the control group for each brain slice.

(iii) Hemispheric brain swelling and infarct volume (the area of dead tissue caused by inadequate blood supply) was measured for test subjects treated with the invention after ischemia, and compared to that of the control group. All three compounds effectively reduced infarct volume (the area of dead tissue caused by inadequate blood supply) and hemispheric brain swelling during ischemic conditions.

The compounds were administered 5 minutes after ischemia, 5 minutes after reperfusion, or 6 hours after ischemia. FIGS. 5a to 5f show results for the heterodimers compound B, C or A respectively, when administered 5 minutes after ischemia or reperfusion. FIGS. 5g and 5h show the results when the novel heterodimers were administered 6 hours after ischemia.

Table 2 indicates that compound B reduced neurological deficits induced by ischemia.

TABLE 2

| Compound | n (dead/total) | Observed Neurological Deficits | | | | Mean ± SEM |
| | | 0 | 1 | 2 | 3 | |
| --- | --- | --- | --- | --- | --- | --- |
| vehicle | 10 (0/10) | 0 | 2 | 8 | 0 | 1.8 ± 0.1 |
| Compound B (0.05 µg/kg) | 9 (2/11) | 0 | 8 | 1 | 0 | 1.1 ± 0.1* |
| Compound B (0.5 µg/kg) | 4 (4/8) | 0 | 2 | 2 | 0 | 1.5 ± 0.3 |

*P < 0.01 when compared with vehicle

Compound B was administered at 5 minutes after ischemia. Distribution of neurological scores based on a four-point scale neurological scoring system (Mann Whitney U test): (0) no observable neurological deficits (normal); (1) failure to extend the left forepaw fully (mild); (2) circling to the contralateral side (moderate); and (3) loss of walking and righting reflex (severe).

Figure 5A:
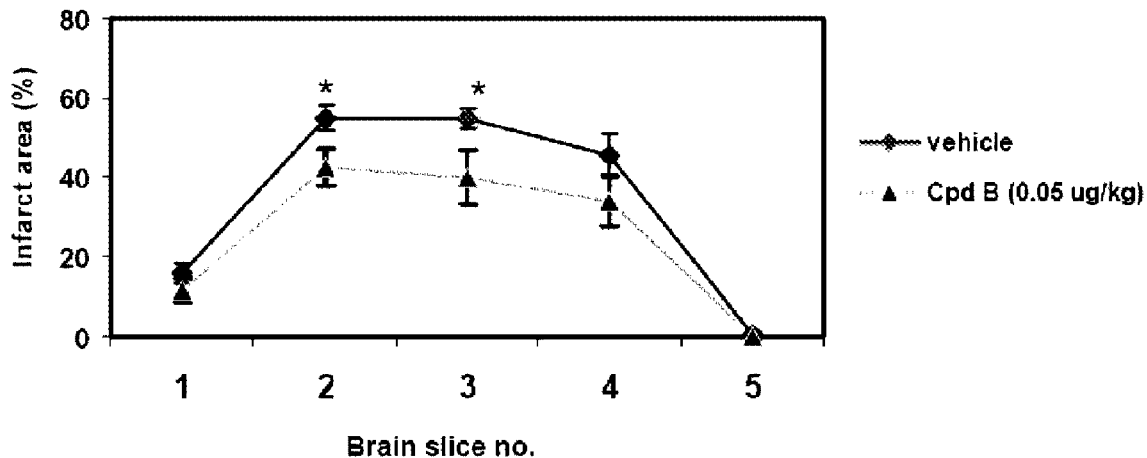
FIGS. 5a to 5h are graphs showing the ability of the claimed compounds to protect subjects against neurological damage.

FIG. 5a demonstrates that compound (cpd) B reduced the infarct area in brain slices #2 and #3 after administration at 0.05 µg/kg. The raw data for FIG. 5a is found in Table 3.

TABLE 3

| | | % Infarct area in brain slice # | | | | |
| | (n) | 1 | 2 | 3 | 4 | 5 |
| --- | --- | --- | --- | --- | --- | --- |
| vehicle | 10 | 15.7 ± 2.5 | 55.1 ± 3.3 | 54.9 ± 2.6 | 45.5 ± 5.4 | 0.5 ± 0.7 |
| Compound B (0.05 µg/kg) | 9 | 11.5 ± 3.0 | 42.6 ± 4.8* | 40.0 ± 6.6* | 34.0 ± 6.5 | 0.1 ± 0.5 |

*P < 0.05

The brain was sectioned into five pieces, each 2-mm thick. The infarct area of each posterior surface was analyzed by an image analysis program. The percentage of infarct area and volume were calculated and presented as the percentage of the infarct area of the contralateral hemisphere to eliminate the contribution of edema to the ischemic lesion.

Figure 5B:
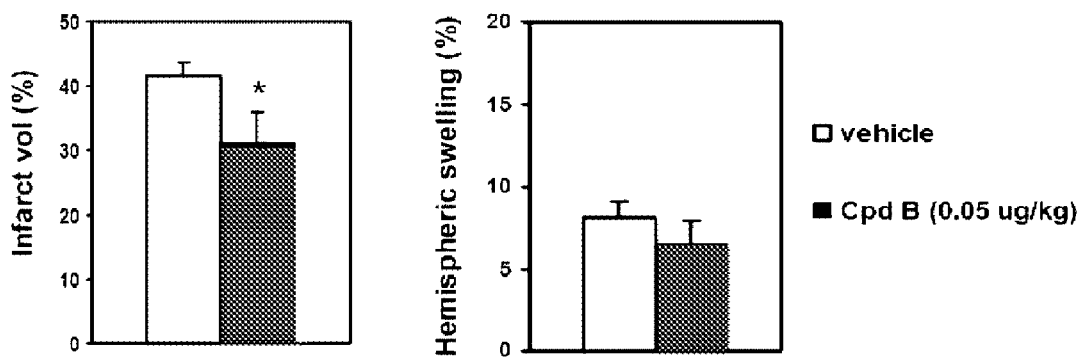

FIG. 5b shows that administration of compound (cpd) B reduces infarct volume but not hemispheric swelling. The raw data for FIG. 5b is found in Table 4.

TABLE 4

| Compound | n | Infarct volume (%) | Hemispheric swelling (%) |
| --- | --- | --- | --- |
| vehicle | 10 | 41.7 ± 1.9 | 8.2 ± 0.9 |
| Compound B (0.05 µg/kg) | 9 | 31.2 ± 4.6* | 6.5 ± 1.5 |

*P < 0.05

The infarct area of each posterior surface was analyzed by an image analysis program. Hemispheric brain swelling was calculated as follows (ipsilateral volume−contralateral volume)/contralateral volume×100%.

Table 5 indicates that compound C reduced neurological deficits induced by ischemia.

TABLE 5

| Compound | n (dead/total) | Observed Neurological Deficits | | | | Mean ± SEM |
| | | 0 | 1 | 2 | 3 | |
| --- | --- | --- | --- | --- | --- | --- |
| vehicle | 7 (4/11) | 0 | 1 | 5 | 1 | 2.0 ± 0.2 |
| Compound C (0.005 µg/kg) | 9 (1/10) | 0 | 9 | 0 | 0 | 1.0 ± 0.0 |
| Compound C (0.05 µg/kg) | 6 (1/7) | 0 | 4 | 2 | 0 | 1.3 ± 0.2 |

Compound C was administered 5 minutes after reperfusion. Distribution of neurological scores based on a four-point scale neurological scoring system (Mann Whitney U test): (0) no observable neurological deficits (normal); (1) failure to extend the left forepaw fully (mild); (2) circling to the contralateral side (moderate); and (3) loss of walking and righting reflex (severe). Note that it was not possible to compute P value (veh vs. 0.005) since SEM for 0.005 µg/kg is 0.

Figure 5C:
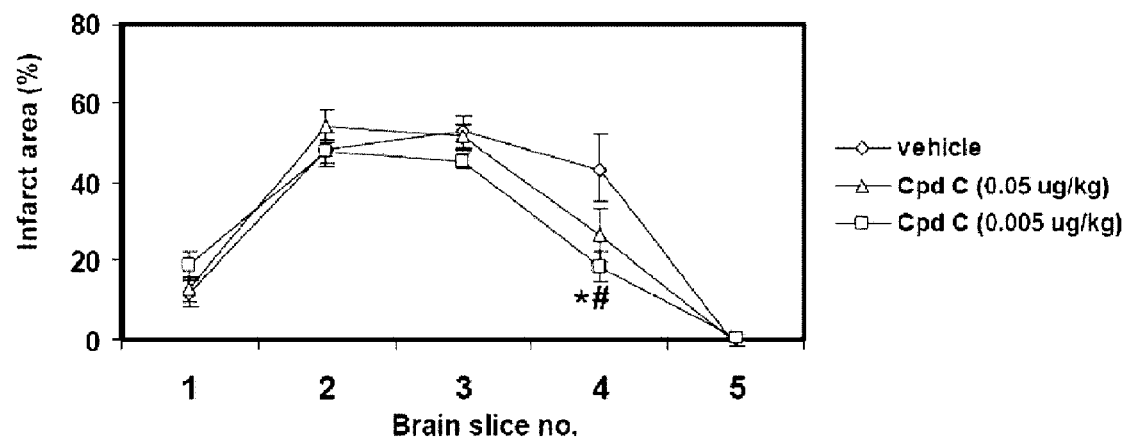

FIG. 5c shows that there was a reduction in infarct area of brain slices #4 after administration of compound (cpd) C 5 minutes after reperfusion. The raw data for FIG. 5c is found in Table 6.

TABLE 6

| Compound | (n) | % Infarct area in brain slice # | | | | |
|---|---|---|---|---|---|---|
| | | 1 | 2 | 3 | 4 | 5 |
| vehicle | 7 | 11.8 ± 3.4 | 48.1 ± 3.6 | 52.6 ± 4.1 | 43.2 ± 8.6 | −1.6 ± 1.1 |
| Compound C (0.005 µg/kg) | 9 | 18.8 ± 3.3 | 47.8 ± 3.0 | 45.4 ± 1.8 | 18.5 ± 3.8*,# | 0.6 ± 0.5 |
| Compound C (0.05 µg/kg) | 6 | 12.8 ± 3.3 | 54.0 ± 4.1 | 51.4 ± 3.1 | 26.2 ± 6.7 | −1.0 ± 0.8 |

*P < 0.01 when compared with vehicle alone (t-test)
P < 0.05 when compared among 3 groups and then with vehicle (ANOVA followed by Bonferroni's post test)

The brain was sectioned into five pieces, each 2-mm thick. The infarct area of each posterior surface was analyzed by an image analysis program. The percentage of infarct area and volume were calculated and presented as the percentage of the infarct area of the contralateral hemisphere to eliminate the contribution of edema to the ischemic lesion.

Figure 5D:
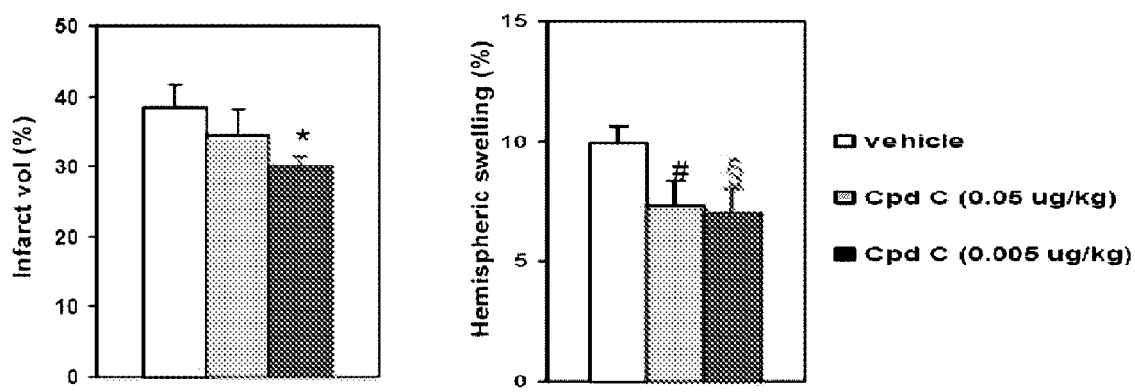

FIG. 5d shows the effect of compound (cpd) C administration 5 minutes after reperfusion reduced infarct size and hemispheric swelling. The raw data for FIG. 5d is found in Table 7.

TABLE 7

| Compound | n | Infarct volume (%) | Hemispheric swelling (%) |
|---|---|---|---|
| vehicle | 7 | 38.4 ± 3.2 | 9.9 ± 0.7 |
| Compound C (0.005 µg/kg) | 9 | 30.1 ± 1.5* | 7.1 ± 1.0§ |
| Compound C (0.05 µg/kg) | 6 | 34.5 ± 3.7 | 7.4 ± 1.0# |

*P < 0.02 when compared to vehicle alone (t-test);
§P < 0.04 when compared to vehicle alone (t-test);
P = 0.0595 when compared with vehicle (t test)

The infarct area of each posterior surface was analyzed by an image analysis program. Hemispheric brain swelling was calculated as follow (ipsilateral volume−contralateral volume)/contralateral volume×100%.

Table 8 indicates that compound A reduced neurological deficits induced by ischemia.

TABLE 8

| Compound | n (dead/total) | Observed Neurological Deficits | | | | Mean ± SEM |
|---|---|---|---|---|---|---|
| | | 0 | 1 | 2 | 3 | |
| vehicle | 10 (8/18) | 0 | 2 | 7 | 1 | 1.9 ± 0.2 |
| Compound A (0.005 mg/kg) | 5 (5/10) | 0 | 2 | 3 | 0 | 1.6 ± 0.2 |
| Compound A (0.05 mg/kg) | 6 (1/7) | 0 | 5 | 1 | 0 | 1.2 ± 0.2* |
| Compound A (0.1 mg/kg) | 9 (4/13) | 0 | 7 | 2 | 0 | 1.2 ± 0.1* |
| Compound A (0.2 mg/kg) | 7 (4/11) | 0 | 2 | 4 | 1 | 1.9 ± 0.7* |

*P < 0.05 when compared with vehicle.

Compound A was administered 5 minutes after ischemia. Distribution of neurological scores based on a four-point scale neurological scoring system (Mann Whitney U test): (0) no observable neurological deficits (normal); (1) failure to extend the left forepaw fully (mild); (2) circling to the contralateral side (moderate); and (3) loss of walking and righting reflex (severe).

Figure 5E:
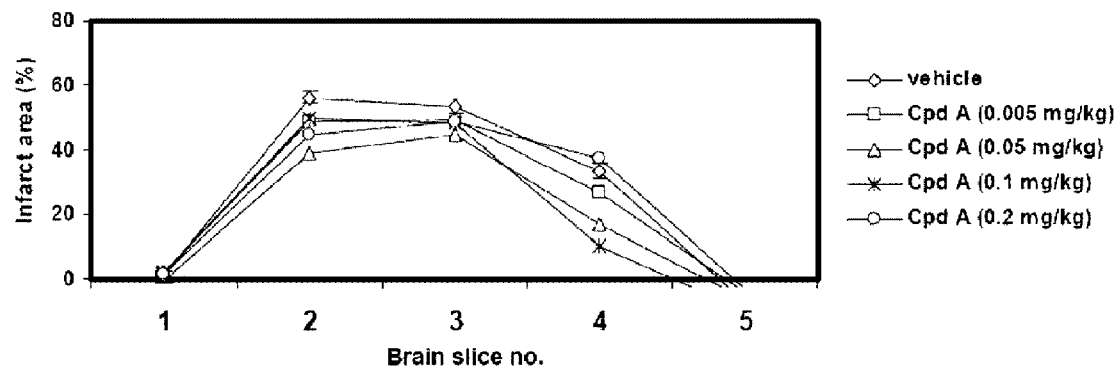

FIG. 5e shows the improvement in the infarct area after administration of compound (cpd) A at dosages of 0.05 and 0.1 mg/kg. The raw data for FIG. 5e is found in Table 9.

TABLE 9

| Compound | (n) | % Infarct area in brain slice # | | | | |
|---|---|---|---|---|---|---|
| | | 1 | 2 | 3 | 4 | 5 |
| vehicle | (10) | 0.8 ± 2.0 | 55.9 ± 1.8 | 53.6 ± 2.1 | 33.5 ± 2.2 | −7.1 ± 1.5 |
| Compound A (0.005 mg/kg) | (5) | 2.2 ± 2.0 | 48.8 ± 4.3 | 49.3 ± 4.4 | 26.5 ± 9.3 | −4.3 ± 0.6 |
| Compound A (0.05 mg/kg) | (6) | −0.4 ± 2.2 | 39.1 ± 2.4** | 44.5 ± 0.9** | 17.1 ± 3.2** | −6.3 ± 2.8 |
| Compound A (0.1 mg/kg) | (9) | 2.0 ± 1.8 | 49.5 ± 2.0* | 48.4 ± 1.8* | 10.4 ± 3.3** | −9.9 ± 1.7 |
| Compound A (0.2 mg/kg) | (7) | 1.3 ± 0.7 | 44.7 ± 6.6 | 49.0 ± 3.8 | 37.3 ± 3.8 | −3.3 ± 1.6 |

(*P = 0.05, **P < 0.01, t test when compared with vehicle)

Compound A was administered 5 minutes after ischemia. The brain was sectioned into five pieces, each 2-mm thick. The infarct area of each posterior surface was analyzed by an image analysis program. The percentage of infarct area and volume were calculated and presented as the percentage of the infarct area of the contralateral hemisphere to eliminate the contribution of edema to the ischemic lesion.

Figure 5F:
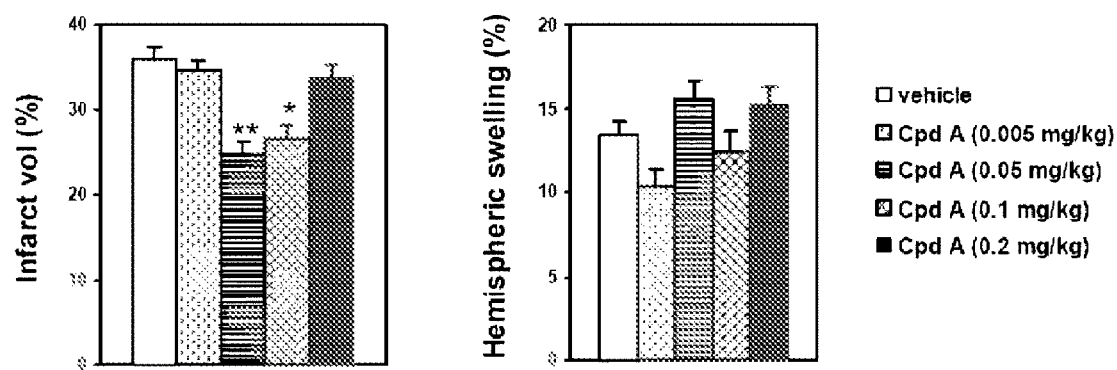
Figure 5G:
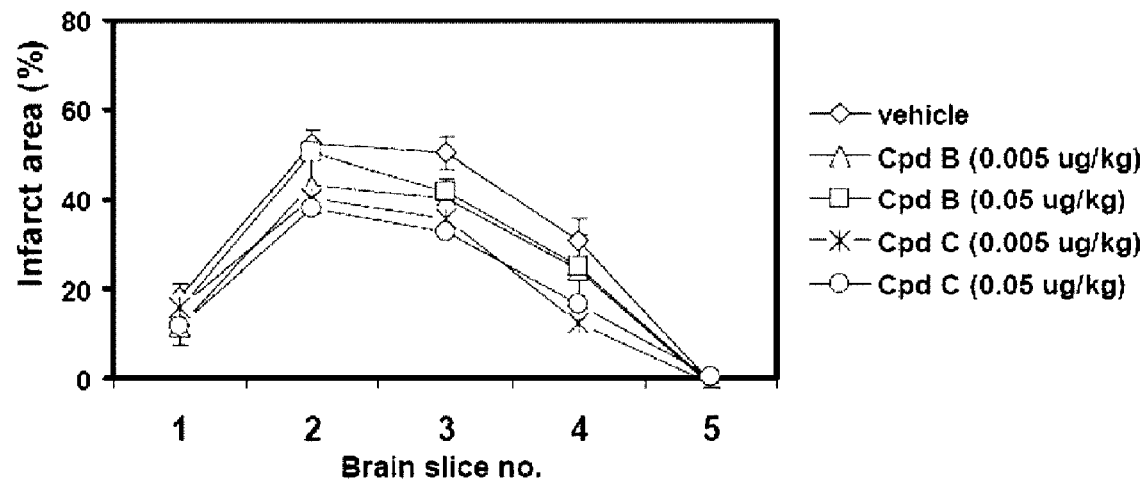
Figure 5H:
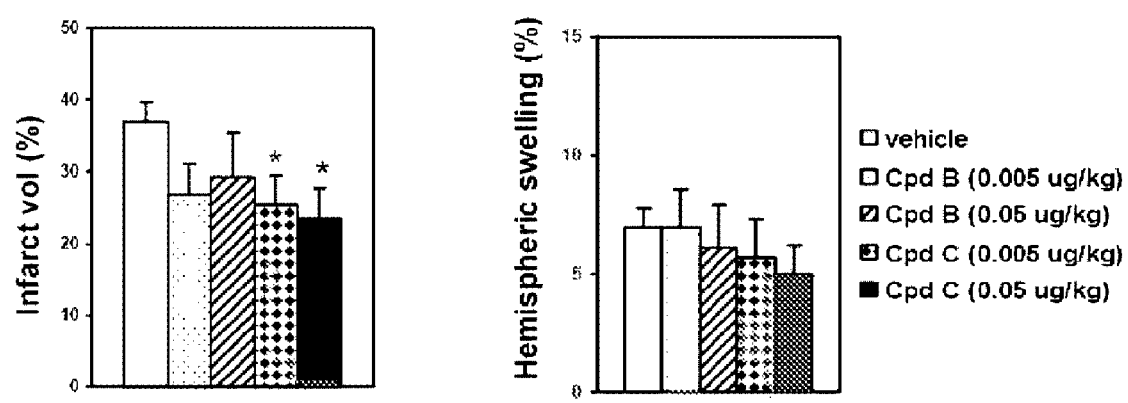

FIG. 5f shows that administration of compound (cpd) A 5 minutes after ischemia (at dosages of 0.05 and 0.1 mg/kg) decreases infarct volume but not hemispheric swelling. The raw data for FIG. 5f is found in Table 10.

Compound B or C was administered 6 hours after ischemia. Distribution of neurological scores based on a four-point scale neurological scoring system (Mann Whitney U test): (0) no observable neurological deficits (normal); (1) failure to extend the left forepaw fully (mild); (2) circling to the contralateral side (moderate); and (3) loss of walking and righting reflex (severe).

FIG. 5g shows that there was an improvement in the infarct area after the administration of compound (cpd) B or C 6 hours after ischemia. The raw data for FIG. 5g is found in Table 12.

TABLE 12

| | | % Infarct area in brain slice # | | | | |
|---|---|---|---|---|---|---|
| Compound | (n) | 1 | 2 | 3 | 4 | 5 |
| vehicle | (10) | 18.3 ± 2.9 | 52.5 ± 2.8 | 50.3 ± 3.6 | 30.6 ± 5.1 | −0.7 ± 0.6 |
| Compound B (0.005 μg/kg) | (9) | 11.9 ± 4.3 | 43.4 ± 6.5 | 40.1 ± 4.7** | 24.3 ± 7.5 | −1.4 ± 1.0 |
| Compound B (0.05 μg/kg) | (8) | 15.7 ± 2.9 | 50.5 ± 7.2 | 41.7 ± 6.0 | 25.2 ± 8.2 | −1.3 ± 1.7 |
| Compound C (0.005 μg/kg) | (8) | 15.9 ± 4.0 | 40.2 ± 7.9 | 35.5 ± 5.3** | 12.5 ± 4.9** | −0.8 ± 0.8 |
| Compound C (0.05 μg/kg) | (8) | 11.7 ± 3.3 | 38.0 ± 6.8* | 32.5 ± 6.6** | 16.8 ± 6.0 | 0.5 ± 0.4 |

*$P < 0.05$,
**$P < 0.03$, t test when compared with control.

TABLE 10

| Compound | n | Infarct volume (%) | Hemispheric swelling (%) |
|---|---|---|---|
| vehicle | (10) | 36.0 ± 1.4 | 13.4 ± 0.8 |
| Compound A (0.005 mg/kg) | (5) | 31.3 ± 4.3 | 10.3 ± 0.4 |
| Compound A (0.05 mg/kg) | (6) | 24.8 ± 1.1** | 15.5 ± 1.1 |
| Compound A (0.1 mg/kg) | (9) | 26.5 ± 1.4* | 12.5 ± 1.1 |
| Compound A (0.2 mg/kg) | (7) | 33.8 ± 1.6 | 15.2 ± 1.2 |

*$P < 0.005$;
**$P < 0.001$ (t test when compared with vehicle)

The infarct area of each posterior surface was analyzed by an image analysis program. Hemispheric brain swelling was calculated as follow (ipsilateral volume−contralateral volume)/contralateral volume×100%.

Table 11 shows that compound B or C reduced neurological deficits upon administration 6 hours after ischemia

TABLE 11

| | n | | Observed Neurological Deficits | | | |
|---|---|---|---|---|---|---|
| Compound | (dead/total) | 0 | 1 | 2 | 3 | Mean ± SEM |
| vehicle | 10 (0/10) | 0 | 1 | 7 | 2 | 2.1 ± 0.2 |
| Compound B (0.005 μg/kg) | 9 (0/9) | 0 | 7 | 2 | 0 | 1.2 ± 0.2** |
| Compound B (0.05 μg/kg) | 8 (3/12) | 0 | 5 | 3 | 0 | 1.4 ± 0.2* |
| Compound C (0.005 μg/kg) | 8 (1/9) | 0 | 6 | 2 | 0 | 1.3 ± 0.2* |
| Compound C (0.05 μg/kg) | 8 (1/9) | 0 | 6 | 2 | 0 | 1.3 ± 0.2* |

*$P < 0.03$,
**$P < 0.01$, Mann Whitney test when compared with control.

The brain was sectioned into five pieces, each 2-mm thick. The infarct area of each posterior surface was analyzed by an image analysis program. The percentage of infarct area and volume were calculated and presented as the percentage of the infarct area of the contralateral hemisphere to eliminate the contribution of edema to the ischemic lesion.

FIG. 5h demonstrates that the administration of compound (cpd) B or C 6 hours after ischemia decreases infarct volume. The raw data for FIG. 5h is found in Table 13.

TABLE 13

| | n | Infarct volume (%) | Hemispheric swelling (%) |
|---|---|---|---|
| vehicle | (10) | 35.8 ± 2.9 | 7.0 ± 0.8 |
| Compound B (0.005 μg/kg) | (9) | 28.5 ± 3.4 | 7.3 ± 1.2 |
| Compound B (0.05 μg/kg) | (8) | 31.1 ± 4.8 | 7.0 ± 1.5 |
| Compound C (0.005 μg/kg) | (8) | 23.9 ± 4.3* | 6.2 ± 1.2 |
| Compound C (0.05 μg/kg) | (8) | 23.5 ± 4.4* | 5.0 ± 1.2 |

*$P < 0.03$ t test when compared with control.

The infarct area of each posterior surface was analyzed by an image analysis program. Hemispheric brain swelling was calculated as follow (ipsilateral volume−contralateral volume)/contralateral volume×100%.

Example 6

The following demonstrates specific methods used in the synthesis of the compounds according to the invention.

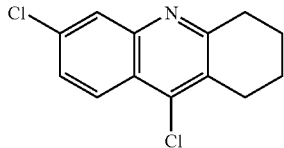

6,9-Dichloro-1,2,3,4-tetrahydro-acridine: To a mixture of 2-amino-4-chlorobenzoic acid (4.5 g, 26.23 mmol) and cyclohexanone (2.72 mL, 26.23 mmoL) was added 22 mL phosphorus oxychloride. The mixture was heated to reflux for 3 hours. The excess phosphorus oxychloride was distilled off and the resulting mixture was treated with saturated sodium bicarbonate. The light brown precipitate was filtered, rinsed with water and dried under vacuum to give the desired product 6.50 g (25.77 mmoL, 98.2%).

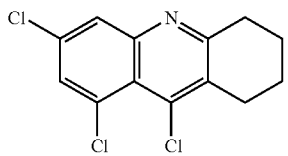

6,8,9-Trichloro-1,2,3,4-tetrahydro-acridine: A mixture of 3,5-dichloro-phenylamine (3.0 g, 18.7 mmoL) and 2-oxo-cyclohexanecarboxylic acid ethyl ester (3.3 mL, 20.5 mmoL) was heated to 90 degree Celsius for 24 h under nitrogen. Phenyl ether (15 mL) was added and the mixture was heated to reflux. The ethanol generated from the reaction was removed by a Dean-Stark trap. After the reaction was completed as shown by TLC, the mixture was allowed to cool to room temperature. Hexane was added and the resulting solid was collected by filtration. Recrystallization of the solid from ethanol afforded the desired product 6,8-dichloro-1,2,3,4-tetrahydro-acridin-9-ol (2.4 g, 48%).

A solution of 6,8-dichloro-1,2,3,4-tetrahydro-acridin-9-ol (18 g, 6.7 mmoL) in phosphorus oxychloride (45 mL) was heated to 135 degree Celsius for 45 min. After the excess phosphorus oxychloride was distilled under vacuum, the remaining mixture was allowed to cool to room temperature and treated with saturated sodium bicarbonate. The resulting suspension was extracted with diethyl ether (×3). The combined ether extract was washed with brine, dried with sodium sulfate, filtered and concentrated. Recrystallization from ethanol afforded the desired product (1.3 g, 68%) as a white solid.

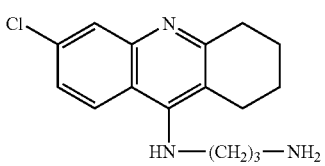

$N^1$-(6-Chloro-1,2,3,4-tetrahydro-acridin-9-yl)-propane-1,3-diamine: To a sealed tube was charged a mixture of 6,9-dichloro-1,2,3,4-tetrahydroacridine (1.0 g, 3.97 mmoL), 1,3-diaminopropane (1.67 mL, 19.83 mmoL) and 4 mL 1-pentanol. The mixture was heated to 160 degree Celsius for 24 h. After cooled down and saturated sodium bicarbonate was added, the mixture was extracted with dichloromethane three times. The combined extract was dried over sodium sulfate, filtered and concentrated. The resulting residue was purified by column chromatography on silica gel with 10-20% MeOH/CH$_2$Cl$_2$ (1% ammonium hydroxide) to give the desired product as brown oil (1.0 g, 87%).

$^1$HNMR (400 MHz, CDCl3): 7.92 (d, J=9.2 Hz, 1H), 7.83 (d, J=2.4 Hz, 1H), 7.21 (dd, J=9.2, 2.4 Hz, 1H), 3.61 (t, J=6.4 Hz, 2H), 2.98 (m, 2H), 2.88 (t, J=6.4 Hz, 2H), 2.62 (m, 2H), 1.87 (m, 4H), 1.77 (m, 2H).

$^{13}$CNMR (100 MHz, CDCl3): 159.1, 150.7, 147.8, 133.5, 127.1, 124.5, 123.6, 118.0, 115.3, 48.3, 40.4, 33.9, 33.8, 24.9, 22.9, 22.6.

The following compounds were prepared according to the procedure described as above by using appropriate diamines and chloro acridines in 80-95% yield:

$N^1$-(6-Chloro-1,2,3,4-tetrahydro-acridin-9-yl)-butane-1,4-diamine;
$N^1$-(6-Chloro-1,2,3,4-tetrahydro-acridin-9-yl)-pentane-1,5-diamine;
$N^1$-(6-Chloro-1,2,3,4-tetrahydro-acridin-9-yl)-hexane-1,6-diamine;
$N^1$-(6-Chloro-1,2,3,4-tetrahydro-acridin-9-yl)-heptane-1,7-diamine;
$N^1$-(6-Chloro-1,2,3,4-tetrahydro-acridin-9-yl)-octane-1,8-diamine;
$N^1$-(6-Chloro-1,2,3,4-tetrahydro-acridin-9-yl)-nonane-1,9-diamine;
$N^1$-(6-Chloro-1,2,3,4-tetrahydro-acridin-9-yl)-decane-1,10-diamine;
$N^1$-(6-Chloro-1,2,3,4-tetrahydro-acridin-9-yl)-dodecane-1,12-diamine;
$N^1$-(6,8-Dichloro-1,2,3,4-tetrahydro-acridin-9-yl)-propane-1,3-diamine;
$N^1$-(6,8-Dichloro-1,2,3,4-tetrahydro-acridin-9-yl)-butane-1,4-diamine;
$N^1$-(6,8-Dichloro-1,2,3,4-tetrahydro-acridin-9-yl)-pentane-1,5-diamine
$N^1$-(6,8-Dichloro-1,2,3,4-tetrahydro-acridin-9-yl)-hexane-1,6-diamine;
$N^1$-(6,8-Dichloro-1,2,3,4-tetrahydro-acridin-9-yl)-heptane-1,7-diamine;
$N^1$-(6,8-Dichloro-1,2,3,4-tetrahydro-acridin-9-yl)-octane-1,8-diamine;
$N^1$-(6,8-Dichloro-1,2,3,4-tetrahydro-acridin-9-yl)-nonane-1,9-diamine;
$N^1$-(6,8-Dichloro-1,2,3,4-tetrahydro-acridin-9-yl)-decane-1,10-diamine; and
$N^1$-(6,8-Dichloro-1,2,3,4-tetrahydro-acridin-9-yl)-dodecane-1,12-diamine.

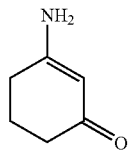

3-Amino-cyclohex-2-enone: To a 1 L two-necked flask charged 200 g (1.78 moL) of 1,3-cyclohexanedione and 600 mL benzene, attached a Dean-Stark apparatus with a condenser and an ammonia inlet. The mixture was heated to reflux and ammonia gas was bubbling into the reaction. The water generated from the reaction was trapped in the Dean-Stark apparatus. The mixture formed two layers and the bottom layer was solidified after refluxing for 4 h. The reaction was then stopped and cooled down to room temperature. The benzene was decanted and the remaining solid was triturated with 300 mL chloroform and filtered to give the desired product as a yellow solid (167.1 g, 1.51 moL, 86%).

1HNMR (400 MHz, CDCl3): 5.23 (s, 1H), 3.20 (bs, 1H), 2.37 (m, 2H), 2.28 (m, 2H), 1.97 (m, 2H).

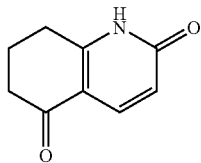

7,8-Dihydro-1H,6H-quinoline-2,5-dione: To a 500 mL flask, added 3-amino-cyclohex-2-enone (110 g, 0.99 moL) and ethyl propiolate (100 mL, 0.99 moL) and attached a condenser. The mixture was heated to 100 degree Celsius. The reaction started slowly at beginning and accelerated as the reaction progress. After the reaction was refluxed at 120 degree Celsius for 4 h, the mixture was heated up to 150 degree Celsius to remove any liquid. Finally, the mixture was heated up to 190 degree Celsius and remained for 1 h. The reaction was cooled to room temperature and 300 mL methylene chloride was added. The mixture was triturated and filtered to give the desired product (34 g, 21%).

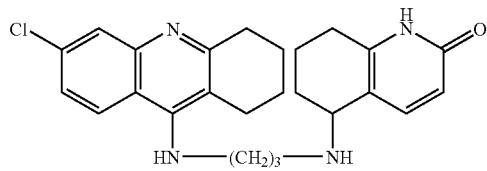

5-[3-(6-Chloro-1,2,3,4-tetrahydro-acridin-9-ylamino)-propylamino]-5,6,7,8-tetrahydro-1H-quinolin-2-one: To a flask was added N1-(6-chloro-1,2,3,4-tetrahydro-acridin-9-yl)-propane-1,3-diamine (116 mg, 0.40 mmoL), 7,8-dihydro-1H,6H-quinoline-2,5-dione (85 mg, 0.52 mmoL), benzene (4 mL) and one drop of acetic acid, and the resulting mixture as heated to reflux under nitrogen. The water generated from the reaction was removed by Dean-Stark apparatus. After refluxing for 24 h, the benzene was distilled off and methanol (2 mL) was added, followed by sodium borohydride (30 mg, 0.80 mmoL). After stiring at room temperature for 24 h, the reaction was stopped and concentrated. The mixture was treated with saturated sodium bicarbonate and methylene chloride. The layers were separated and the aqueous layer was extracted with methylene chloride twice. The combined methylene chloride extract was combined, dried over sodium sulfate, filtered and concentrated. The resulting residue was purified by preparative TLC using 15% MeOH/1% ammonium hydroxide in methylene chloride to give the desired product (102 mg, 0.23 mmoL, 58%).

¹HNMR (400 MHz, CDCl₃): δ 7.86 (d, J=9.0 Hz, 1H), 7.84 (d, J=1.8 Hz, 1H), 7.41 (d, J=9.0 Hz, 1H), 7.19 (dd, J=9.0, 1.8 Hz, 1H), 6.36 (d, J=9.0 Hz, 1H), 3.62 (t, J=6.0 Hz, 2H), 3.53 (m, 1H), 2.96 (m, 2H), 2.89 (m, 1H), 2.75 (m, 1H), 2.63 (m, 4H), 1.74-1.83 (m, 10H).

¹³CNMR (100 MHz, CDCl₃): δ 164.8, 159.1, 150.9, 147.7, 144.2, 143.1, 133.8, 127.1, 124.5, 123.9, 118.1, 116.9, 116.8, 115.5, 53.2, 48.6, 45.4, 33.8, 31.8, 27.2, 26.8, 25.0, 22.9, 22.6, 17.3.

The following compounds were prepared according to the procedures described above:

5-[5-(6-Chloro-1,2,3,4-tetrahydro-acridin-9-ylamino)-pentylamino]-5,6,7,8-tetrahydro-1H-quinolin-2-one (he-3-100)

¹HNMR (400 MHz, CDCl₃): δ 7.89 (m, 2H), 7.51 (m, 1H), 7.35 (d, J=8.4 Hz, 1H), 6.37 (d, J=9.2 Hz, 1H), 3.95 (bs, 1H), 3.59 (m, 1H), 3.50 (m, 3H), 3.03 (m, 2H), 2.66 (m, 6H), 1.91 (m, 6H), 1.67-1.79 (m, 4H), 1.57 (m, 2H), 1.25 (m, 2H).

5-[6-(6-Chloro-1,2,3,4-tetrahydro-acridin-9-ylamino)-hexylamino]-5,6,7,8-tetrahydro-1H-quinolin-2-one (he-3-101)

¹HNMR (400 MHz, CDCl₃): δ 7.90 (d, J=9.2 Hz, 1H), 7.88 (s, 1H), 7.52 (d, J=9.2 Hz, 1H), 7.27 (m, 1H), 6.40 (d, J=9.2 Hz, 1H), 3.95 (brs, 1H), 3.55 (m, 1H), 3.49 (m, 3H), 3.03 (m, 2H), 2.68 (m, 4H), 2.60 (m, 2H), 1.92 (m, 6H), 1.78 (m, 2H), 1.67 (m, 2H), 1.50 (m, 2H), 1.41 (m, 4H)

5-[7-(6-Chloro-1,2,3,4-tetrahydro-acridin-9-ylamino)-heptylamino]-5,6,7,8-tetrahydro-1H-quinolin-2-one (he-3-102)

¹HNMR (400 MHz, CDCl₃): δ 7.88 (d, J=9.2 Hz, 1H), 7.87 (s, 1H), 7.48 (d, J=9.2 Hz, 1H), 7.27 (m, 1H), 6.39 (d, J=9.2 Hz, 1H), 3.95 (brs, 1H), 3.53 (m, 1H), 3.47 (m, 3H), 3.02 (m, 2H), 2.66 (m, 4H), 2.58 (m, 2H), 1.91 (m, 6H), 1.77 (m, 2H), 1.65 (m, 2H), 1.46 (m, 2H), 1.34 (m, 6H).

¹³CNMR (100 MHz, CDCl₃): δ 164.8, 159.2, 150.5, 147.9, 144.0, 143.1, 133.6, 127.3, 124.3, 123.9, 118.2, 117.2, 116.7, 115.5, 52.9, 49.5, 46.9, 34.0, 31.7, 30.4, 29.2, 27.5, 27.2, 26.8, 26.8, 24.5, 22.9, 22.6, 17.4.

5-[8-(6-Chloro-1,2,3,4-tetrahydro-acridin-9-ylamino)-octylamino]-5,6,7,8-tetrahydro-1H-quinolin-2-one (he-3-103)

¹HNMR (400 MHz, CDCl₃): δ 7.88 (d, J=9.2 Hz, 1H), 7.87 (s, 1H), 7.48 (d, J=9.2 Hz, 1H), 7.27 (m, 1H), 6.39 (d, J=9.2 Hz, 1H), 4.05 (brs, 1H), 3.59 (m, 1H), 3.48 (m, 3H), 3.03 (m, 2H), 2.67 (m, 6H), 1.91 (m, 6H), 1.78 (m, 2H), 1.65 (m, 2H), 1.50 (m, 2H), 1.32 (m, 8H)

5-[9-(6-Chloro-1,2,3,4-tetrahydro-acridin-9-ylamino)-nonylamino]-5,6,7,8-tetrahydro-1H-quinolin-2-one (he-3-104Lh)

¹HNMR (400 MHz, CDCl₃): δ 7.89 (d, J=9.2 Hz, 1H), 7.88 (s, 1H), 7.48 (d, J=9.2 Hz, 1H), 7.26 (m, 1H), 6.40 (d, J=9.2 Hz, 1H), 3.95 (brs, 1H), 3.54 (m, 1H), 3.48 (m, 2H), 3.02 (m, 2H), 2.67 (m, 4H), 2.59 (m, 2H), 1.91 (m, 6H), 1.78 (m, 2H), 1.65 (m, 2H), 1.48 (m, 2H), 1.32 (m, 10H)

5-[10-(6-Chloro-1,2,3,4-tetrahydro-acridin-9-ylamino)-decanylamino]-5,6,7,8-tetrahydro-1H-quinolin-2-one (he-3-105Lh)

¹HNMR (400 MHz, CDCl₃): δ 7.90 (d, J=9.2 Hz, 1H), 7.88 (s, 1H), 7.49 (d, J=9.2 Hz, 1H), 7.26 (m, 1H), 6.40 (d, J=9.2 Hz, 1H), 3.95 (brs, 1H), 3.55 (m, 1H), 3.47 (m, 2H), 3.02 (m, 2H), 2.67 (m, 4H), 2.59 (m, 2H), 1.91 (m, 6H), 1.75 (m, 2H), 1.64 (m, 2H), 1.47 (m, 2H), 1.32 (m, 12H)

5-[12-(6-Chloro-1,2,3,4-tetrahydro-acridin-9-ylamino)-dodecanylamino]-5,6,7,8-tetrahydro-1H-quinolin-2-one (he-3-109)

¹HNMR (400 MHz, CDCl₃): δ 7.90 (d, J=9.2 Hz, 1H), 7.88 (s, 1H), 7.49 (d, J=9.2 Hz, 1H), 7.26 (m, 1H), 6.40 (d, J=9.2

Hz, 1H), 3.95 (brs, 1H), 3.55 (m, 1H), 3.48 (m, 2H), 3.02 (m, 2H), 2.67 (m, 4H), 2.59 (m, 2H), 1.91 (m, 6H), 1.75 (m, 2H), 1.64 (m, 2H), 1.47 (m, 2H), 1.32 (m, 16H)

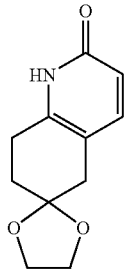

1,5,7,8-Tetrahydro-quinoline-2,6-dione 6-ethylene glycol ketal: A mixture of 1,4-cyclohexanedione mono-ethylene ketal (10 g, 64 mmoL) and methyl propiolate (6.8 mL, 76.8 mmoL) in 60 mL ammonium saturated methnol was heated to 110 degree Celsius in a sealed pressure vessel for 24 h. The reaction was cooled to room temperature and concentrated. Purification by column chromatography on silica gel with 5% methanol in methylene chloride provided the desired product (4.1 g, 19.6 mmoL, 31%).

$^1$HNMR (300 MHz, CDCl$_3$): δ 7.18 (d, J=9.2 Hz, 1H), 6.42 (d, J=9.2 Hz, 1H), 4.01 (s, 4H), 2.91 (t, J=6.6 Hz, 2H), 2.71 (s, 2H), 1.92 (t, J=6.7 Hz, 2H).

$^{13}$CNMR (75 MHz, CDCl$_3$): δ 164.9, 143.5, 141.9, 117.2, 112.2, 107.3, 64.6, 36.2, 30.1, 25.7.

MS (ESI) 208.26 (M+H).

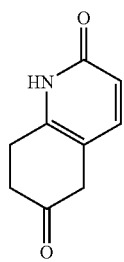

1,5,7,8-Tetrahydro-quinoline-2,6-dione: A mixture of 1,5,7,8-Tetrahydro-quinoline-2,6-dione 6-ethylene glycol ketal (2 g, 9.66 mmoL) and p-toluenesulfonic acid monohydrate (184 mg, 0.97 mmoL) in 30 mL water was heated to reflux for 3 h. TLC showed all the starting ketal disappeared. The mixture was cooled down to room temperature, and sodium bicarbonate was added. The mixture was concentrated and silica gel was added. Purification by column chromatography on silica gel with 5% methanol/methylene chloride provided the desired product in 90% yield.

$^1$HNMR (300 MHz, CDCl$_3$): δ 7.25 (d, J=9.1 Hz, 1H), 6.49 (d, J=9.1 Hz, 1H), 3.36 (s, 2H), 3.11 (t, J=7.0 Hz, 2H), 2.65 (t, J=7.0 Hz, 2H).

$^{13}$CNMR (75 MHz, CDCl$_3$): δ 207.1, 165.0, 142.8, 142.2, 118.1, 111.2, 40.3, 36.9, 26.0.

MS (ESI): 164.20 (M+H).

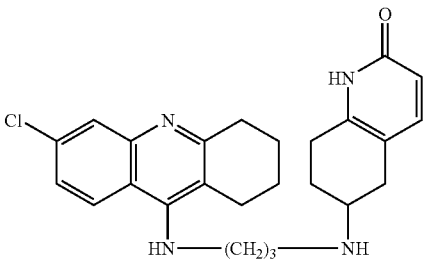

6-[3-(6-Chloro-1,2,3,4-tetrahydro-acridin-9-ylamino)-propylamino]-5,6,7,8-tetrahydro-1H-quinolin-2-one: To a mixture of N1-(6-Chloro-1,2,3,4-tetrahydro-acridin-9-yl)-propane-1,3-diamine (50 mg, 0.17 mmoL), 1,5,7,8-Tetrahydro-quinoline-2,6-dione (31 mg, 0.19 mmoL) in 5 mL methylene chloride, was added sodium triacetoxyborohydride (110 mg, 0.52 mmoL) and a catalytic amount of acetic acid. After stiring at room temperature for 24 h, the reaction was stopped by adding saturated sodium bicarbonate. The mixture was extracted with methylene chloride three times. The combined methylene chloride extract was dried, filtered and concentrated. Purification by column chromatography on silica gel column with 10% MeOH/1% ammonium hydroxide in methylene chloride provided the desired product (27.6 mg, 0.063 mmoL, 37%).

Mp: 98-100 C.

IR(KBr): 3422, 2931, 1633, 1605, 1447, 1361, 1092, 831.

$^1$H NMR (CDCl$_3$/CD$_3$OD): δ 1.72 (m, 1H); 1.88 (m, 6H); 2.07 (m, 1H); 2.42 (m, 1H); 2.53-2.61 (m, 6H); 2.93-2.99 (m, 4H); 3.75 (m, 2H); 6.37 (d, 1H, J=8.8 Hz); 7.20 (d, 1H, J=9.2 Hz); 7.25 (dd, J=9.2, 2.4 Hz, 1H); 7.84 (d, J=2.4 Hz, 1H); 7.99 (d, J=9.2 Hz, 1H).

$^{13}$C NMR (CDCl$_3$/CD$_3$OD): δ 21.9; 22.5; 23.9; 24.9; 26.9; 29.0; 30.5; 31.9; 32.5, 34.4; 45.3; 52.9; 65.0; 112.4; 114.3; 116.8; 117.0; 124.3; 125.0; 135.2; 141.6; 143.7; 144.1, 145.1; 152.2; 156.8; 164.0.

MS(ESI): 437.31 (M+H).

The following compounds were prepared according to the procedure described above:

6-[9-(6-Chloro-1,2,3,4-tetrahydro-acridin-9-ylamino)-nonylamino]-5,6,7,8-tetrahydro-1H-quinolin-2-one Mp: 163-165 C.

IR(KBr): 3418, 2929, 2854, 1630, 1449, 1092, 832.

$^1$H NMR (400 MHz, CDCl$_3$/CD$_3$OD): δ 1.30 (m, 6H); 1.58-1.69 (m, 8H); 1.92 (m, 6H); 2.12 (m, 1H); 2.47 (m, 1H); 2.65-2.82 (m, 8H); 3.00 (m, 2H); 3.58 (m, 2H); 6.37 (d, J=9.2 Hz, 1H); 7.23 (d, J=9.2 Hz, 1H); 7.30 (dd, J=9.2, 2.4 Hz, 1H); 7.85 (d, J=2.4 Hz, 1H); 7.98 (d, J=9.2 Hz, 1H).

$^{13}$C NMR (75 MHz, CDCl$_3$/CD$_3$OD): δ 22.0; 22.5; 24.2; 25.0; 26.3; 26.6; 27.0; 28.6; 29.0; 29.1; 29.2; 31.3; 32.3; 46.3; 48.4; 49.2; 52.6; 112.1; 114.4; 117.0; 117.1; 124.2; 124.7; 124.8; 134.8; 141.3; 143.6; 145.8; 151.8; 157.5; 163.8.

MS(ESI): 521.46 (M+H).

6-[8-(6-Chloro-1,2,3,4-tetrahydro-acridin-9-ylamino)-octylamino]-5,6,7,8-tetrahydro-1H-quinolin-2-one Mp: 185-187 C.

IR(KBr): 3400, 2990, 2856, 1649, 1630, 1605, 1518, 1452, 1357, 1179, 1092, 830.

$^1$H NMR (CDCl$_3$/CD$_3$OD): δ 1.33 (m, 8H); 1.58-1.69 (m, 6H); 1.92 (m, 4H); 2.12 (m, 1H); 2.47 (m, 2H); 2.65-2.83 (m, 7H); 3.01 (br, 3H); 6.37 (d, J=9.2 Hz, 1H); 7.22 (d, J=9.2 Hz, 1H); 7.30 (m, 1H); 7.87 (m, 1H); 7.98 (d, J=9.2 Hz, 1H).

¹³C NMR (CDCl₃/CD₃OD): δ 22.0; 22.5; 24.3; 25.0; 26.3; 26.6; 26.9; 28.6; 29.0; 29.1; 31.3; 31.4; 32.3; 46.4; 48.6; 52.7; 112.1; 114.5; 117.1; 117.2; 124.3; 124.8; 124.8; 135.0; 141.2; 143.7; 145.7; 151.9; 157.4; 163.8.

MS(ESI): 507.38 (M+H).

6-[7-(6-Chloro-1,2,3,4-tetrahydro-acridin-9-ylamino)-heptylamino]-5,6,7,8-tetrahydro-1H-quinolin-2-one Mp: 126-127 C.

IR(KBr): 3423, 2930, 1629, 1450, 1092, 831.

¹H NMR (CDCl₃/CD₃OD): δ 1.38 (br, 6H); 1.59-1.70 (m, 6H); 1.92 (br, 4H); 2.12 (m, 1H); 2.47 (m, 2H); 2.66-2.78 (m, 7H); 3.01 (br, 3H); 6.37 (d, J=9.2 Hz, 1H); 7.22 (d, J=9.2 Hz, 1H); 7.30 (m, 1H); 7.86 (s, 1H); 7.98 (d, J=9.2 Hz, 1H).

¹³C NMR (CDCl₃/CD₃OD): δ22.0; 22.5; 24.3; 25.0, 26.3; 26.6; 26.9; 28.5; 28.9; 31.2; 31.4; 32.2; 46.3; 48.5; 52.7; 112.1; 114.5; 117.0; 117.2; 124.4; 124.7; 124.8; 135.0; 141.2; 143.6; 145.6; 151.9; 157.4; 163.8.

MS(ESI): 493.37 (M+H).

6-[6-(6-Chloro-1,2,3,4-tetrahydro-acridin-9-ylamino)-hexylamino]-5,6,7,8-tetrahydro-1H-quinolin-2-one Mp: 147-149 C.

IR(KBr): 3423, 2930, 1634, 1459, 1092, 829.

¹H NMR (CDCl₃/CD₃OD): δ 1.42 (m, 4H); 1.59-1.71 (m, 5H); 1.92 (m, 5H); 2.11 (m, 2H); 2.43 (m, 1H); 2.67-2.73 (m, 8H); 3.00 (br, 3H); 3.57 (m, 3H); 6.38 (d, 1H, J=8.8 Hz); 7.23 (d, 1H, J=9.2 Hz); 7.30 (m, 1H); 7.85 (m, 1H); 7.97 (d, 1H, J=9.2 Hz).

¹³C NMR (CDCl₃/CD₃OD): δ 22.1; 22.5; 23.9; 24.3; 25.0; 26.5; 26.7; 28.9; 31.2; 31.8; 32.5; 34.3; 46.3; 52.7; 112.3; 114.7; 117.0; 124.2; 124.7; 125.0; 134.7; 141.4; 143.7; 146.1; 146.0; 151.6; 157.7; 163.9

MS(ESI): 479.36 (M+H).

6-[10-(6-Chloro-1,2,3,4-tetrahydro-acridin-9-ylamino)-decanylamino]-5,6,7,8-tetrahydro-1H-quinolin-2-one Mp: 161-163 C.

IR(KBr): 3411, 2929, 2854, 1630, 1450, 1360, 1092, 832.

¹H NMR (CDCl₃/CD₃OD): δ1.28 (m, 12H); 1.58-1.68 (m, 5H); 1.91 (m, 5H); 2.14 (m, 1H); 2.47 (m, 1H); 2.65-2.78 (m, 6H); 3.01 (br, 3H); 3.55 (m, 3H); 6.36 (d, J=9.2 Hz, 1H); 7.20 (d, J=9.2 Hz, 1H); 7.29 (m, 1H); 7.87 (m, 1H); 7.95 (d, J=9.2 Hz, 1H).

¹³C NMR (CDCl₃/CD₃OD): δ 22.2; 22.7; 24.3; 25.1; 26.4; 26.8; 27.1; 28.8; 29.2; 29.3; 29.3; 29.3; 29.3; 31.5; 31.5; 32.7; 46.5; 52.7; 112.1; 114.6; 117.2; 117.3; 124.3; 124.7; 125.4; 134.7; 141.3; 143.7; 146.3; 151.6; 158.0; 164.0.

MS (ESI): 535.37 (M+H).

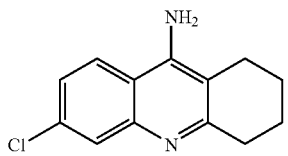

6-Chloro-1,2,3,4-tetrahydro-acridin-9-ylamine: 2-Amino-4-chlorobenzonitrile (5.0 g, 33 mmoL), cyclohexanone (30 ml) and Zinc chloride (4.8 g, 35 mmoL) were mixed in a round bottomed flask and heated up to 120 degree Celsius for 3 hours. After cooling to room temperature, the solvent was decanted off. The resulting residue was triturated with ethyl acetate (30 ml). The solid was collected by filtration and added into 10% aqueous NaOH (50 ml). After stiring for 2 hours, the mixture was filtered and the filter cake was washed thoroughly with water. The filter cake was then extracted with methanol. The combined methanolic extract was concentrated to produce the desired product (3.8 g, 16 mmoL) in 48% yield.

¹HNMR (300 MHz, CD₃OD): δ 8.06 (d, J=9.0 Hz, 1H), 7.68 (d, J=2.1 Hz, 1H), 7.33 (dd, J=9.0, 2.1 Hz, 1H), 2.92 (t, J=6.0 Hz, 2H), 2.61 (t, J=6.0 Hz, 2H), 1.94 (m, 4H).

MS (ESI): 233 [M+1]

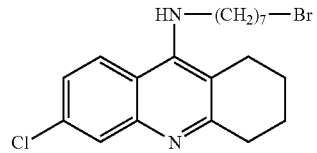

(7-Bromo-heptyl)-(6-chloro-1,2,3,4-tetrahydro-acridin-9-yl)-amine: Potassium hydroxide (95 mg, 1.7 mmoL) was added to a solution of 6-chloro-1,2,3,4-tetrahydro-acridin-9-ylamine (395 mg, 1.7 mmoL) in dimethylsulfoxide (15 ml) and the mixture was stirred vigorously under nitrogen at room temperature for 2 h. 1,7-Dibromoheptane (438 mg, 1.7 mmoL) was added, and the reaction was continued to stir at room temperature for 12 h. The reaction mixture was poured into ice-water and extracted with ethyl acetate. The combined ethyl acetate extract was dried, filtered and concentrated. The resulting residue was purified by column chromatography on silica gel using hexane/ethyl acetate/triethyl amine (8/2/1) to provide the desired product (244 mg, 0.60 mmoL) in 35% yield.

¹HNMR (300 MHz, CDCl₃): δ 7.87 (m, 2H), 7.24 (dd, J=9.0, 2.1 Hz, 1H), 3.62 (t, J=6.9 Hz, 2H), 3.54 (t, J=6.6 Hz, 2H), 3.18 (bs, 2H), 2.81 (bs, 2H), 1.23~2.04 (m, 14H);

¹³CNMR (75 MHz, CDCl₃): δ 159.4, 150.6, 148.0, 133.7, 127.5, 124.5, 123.9, 118.3, 115.6, 49.4, 33.9, 33.7, 32.5, 31.5, 28.3, 27.8, 26.6, 24.4, 22.8, 22.5.

The following compounds were prepared according to the procedure described above:

(8-Bromo-octyl)-(6-chloro-1,2,3,4-tetrahydro-acridin-9-yl)-amine

¹HNMR (400 MHz, CDCl₃): δ 7.88 (m, 2H), 7.26 (dd, J=9.3, 1.9 Hz, 1H), 3.46 (t, J=7.2 Hz, 2H), 3.39 (t, J=6.8 Hz, 2H), 3.02 (brs, 2H), 2.65 (brs, 2H), 1.25~1.91 (m, 16H);

¹³CNMR (75 MHz, CDCl₃): δ 159.3, 150.5, 147.9, 133.7, 127.4, 124.4, 123.9, 118.2, 115.5, 49.5, 34.0, 33.9, 32.7, 31.7, 29.1, 28.6, 28.0, 26.8, 24.6, 23.0, 22.7.

(9-Bromo-nonyl)-(6-chloro-1,2,3,4-tetrahydro-acridin-9-yl)-amine

¹H-NMR (400 MHz CDCl₃): δ 7.87 (m, 2H), 7.24 (dd, J=9.0, 2.0 Hz, 1H), 3.45 (m, 2H), 3.38 (t, J=6.8 Hz, 2H), 3.01 (brs, 2H), 2.64 (brs, 2H), 1.23~1.90 (m, 17H).

¹³C-NMR (75 MHz, CDCl₃): δ 159.1, 150.5, 147.8, 133.6, 127.2, 124.4, 123.8, 118.1, 115.4, 49.5, 34.0, 33.9, 32.7, 31.7, 29.2, 29.1, 28.6, 28.0, 26.8, 24.5, 22.9, 22.6.

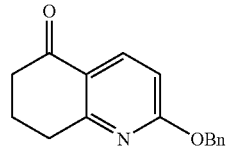

2-Benzyloxy-7,8-dihydro-6H-quinolin-5-one: A mixture of 7,8-dihydro-1H,6H-quinoline-2,5-dione (20.4 g, 125.0 mmoL), benzyl bromide (17.8 mL, 150 mmoL) and 20.8 g, 75 mmoL) in toluene (250 mL) was stirred at room temperature for 3 days under the protection from light. The reaction was stopped, filtered through celite and rinsed with a mixture of methylene chloride and methanol. The filtrate was concentrated and triturated in petroleum ether (150 mL). Filtration of the mixture provided the desired product (29.4 g, 92%).

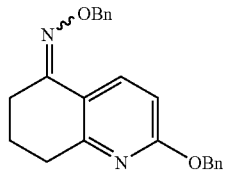

O-Benzyl-N-(2-benzyloxy-5,6,7,8-tetrahydro-quinolin-5-yl)-hydroxylamine: To the mixture of 2-benzyloxy-7,8-dihydro-6H-quinolin-5-one (37.8 g, 149 mmol) in pyridine (300 mL) was added O-benzylhydroxylamine hydrochloride (26.2 g, 164 mmol) and the resulting mixture was stirred at room temperature for 24 h. The reaction was concentrated, diluted with methylene chloride and washed with saturated sodium bicarbonate (×2) and brine (×2). The methylene chloride layer was dried, filtered and concentrated. Purification by column chromatography on silica gel with 5% ethyl acetate in hexane provided the desired product (51.0 g, 96%) as an offwhite solid.

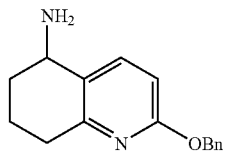

2-Benzyloxy-5,6,7,8-tetrahydro-quinolin-5-ylamine: A solution of O-benzyl-N-(2-benzyloxy-5,6,7,8-tetrahydro-quinolin-5-yl)-hydroxylamine (51.0 g, 142 mmol) dissolved in dry THF (65 mL) was cooled in ice-water bath under nitrogen. Borane (1.0 M in THF, 427 mL) was added dropwise in 30 min via an addition funnel. The reaction was allowed to warm up to room temperature and stirred for overnight. The mixture was then heated to reflux. After 2 h, the heating was stopped and the reaction was allowed to cool to room temperature. Water (120 mL) was added dropwise via an addition funnel. The mixture was then concentrated, and 20% aqueous sodium hydroxide (200 mL) was added. The resulting mixture was heated to reflux for 2 h. The reaction was allowed to cool to room temperature, and extracted with methylene chloride (×3). The combined methylene chloride extract was dried, filtered and concentrated. Purification by column chromatography on silica gel with 20% methanol/1% ammonium hydroxide/methylene chloride provided the desired product (32.0 g, 89%) as colorless oil.

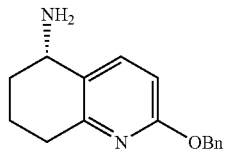

(S)-2-Benzyloxy-5,6,7,8-tetrahydro-quinolin-5-ylamine

Resolution: To a solution of R-(−)-mandelic acid (26.64 g, 104.8 mmol) dissolved in 700 mL methanol, was added a solution of racemic 2-benzyloxy-5,6,7,8-tetrahydro-quinolin-5-ylamine (15.95 g, 104.8 mmol) dissolved in 100 mL methanol. After addition was completed, additional methanol was added until the total volume is 0.95 L. The solution was swirled and allowed to sit at room temperature overnight. The salt of R-(−)mandelic acid and (S)-2-benzyloxy-5,6,7,8-tetrahydro-quinolin-5-ylamine was crystallized. The crystals (15.8 g, 36.6%) were collected by filtration and rinse with methanol. Its optical purity was determined to be 94% ee. The crystals were dissolved again in 760 mL methanol upon heating and the resulting solution was allowed to sit at room temperature overnight. The needle crystals (9.6 g, 22%, 97% ee) were collected by filtration. Another crop (3.6 g, 8.5%, 98% ee) was obtained from the mother liquor.

Releasing: The salt of R-(−)mandelic acid and (S)-2-benzyloxy-5,6,7,8-tetrahydro-quinolin-5-ylamine (13.29 g, ~98% ee) was added to into a solution of aqueous sodium hydroxide (82 mL, 2 N), and the resulting mixture was heated to 50 degree Celsius for 30 min. The mixture was extracted with methylene chloride (×3). The combined methylene chloride was washed with brine (×1), dried over sodium sulfate, filtered and concentrated to give the desired product (8.3 g) as colorless oil.

(R)-2-Benzyloxy-5,6,7,8-tetrahydro-quinolin-5-ylamine: According to the procedure described as above, using S-(+)-mandelic acid as resolution reagent, the desired (R)-enantiomer was obtained.

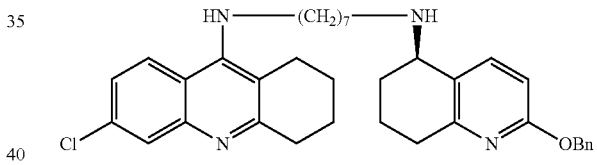

(R)—N-(2-Benzyloxy-5,6,7,8-tetrahydro-quinolin-5-yl)-N'-(6-chloro-1,2,3,4-tetrahydro-acridin-9-yl)-heptane-1,7-diamine: A solution of (7-bromo-heptyl)-(6-chloro-1,2,3,4-tetrahydro-acridin-9-yl)-amine (180 mg, 0.43 mmol) and (S)-2-benzyloxy-5,6,7,8-tetrahydro-quinolin-5-ylamine (108 mg, 0.43 mmol) in dried N,N-dimethylformamide (2.1 ml) was heated up to 120 degree Celsius under nitrogen for 5 h. After cooling to room temperature, the reaction mixture was poured into icy water. The mixture was extracted with ethyl acetate. The combined ethyl acetate was dried, filtered and concentrated. The resulting crude product was purified by column chromatography on silica gel using hexane/ethyl acetate/triethyl amine (8/2/1) to give the desired product (80 mg, 0.14 mmol) in 33% yield.

$^1$HNMR (400 MHz, CDCl$_3$): δ 7.88 (m, 2H), 7.24~7.56 (m, 7H), 6.58 (d, J=8.3 Hz, 1H), 5.33 (s, 2H), 3.68 (d, J=4.4 Hz, 1H), 3.45 (d, J=5.6 Hz, 2H), 3.01 (brs, 2H), 2.56~2.82 (m, 6H), 1.31~1.98 (m, 18H).

$^{13}$C-NMR (100 MHz, CDCl$_3$): δ 161.5, 159.4, 154.5, 150.6, 148.0, 139.5, 137.5, 133.7, 128.2 (2C), 127.9 (2C), 127.5, 127.4, 127.2, 124.4, 124.0, 118.3, 115.6, 108.2, 67.4, 54.6, 49.6, 47.0, 34.1, 32.4, 31.8, 30.5, 29.3, 28.2, 27.4, 27.0, 24.6, 23.0, 22.7, 18.9.

The following compounds were prepared according to the procedure described above.

(S)—N-(2-Benzyloxy-5,6,7,8-tetrahydro-quinolin-5-yl)-N'-(6-chloro-1,2,3,4-tetrahydro-acridin-9-yl)-heptane-1,7-diamine

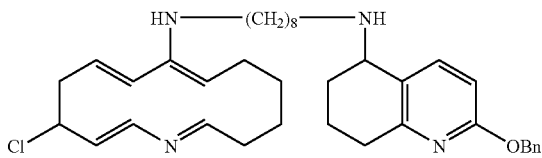

(S)—N-(2-Benzyloxy-5,6,7,8-tetrahydro-quinolin-5-yl)-N'-(6-chloro-1,2,3,4-tetrahydro-acridin-9-yl)-Octane-1,8-diamine (R)—N-(2-Benzyloxy-5,6,7,8-tetrahydro-quinolin-5-yl)-N'-(6-chloro-1,2,3,4-tetrahydro-acridin-9-yl)-Octane-1,8-diamine $^1$HNMR (400 MHz, CDCl$_3$): δ 7.24~7.89 (m, 9H), 6.59 (dd, J=8.3, 5.6 Hz, 1H), 5.33 (s, 2H), 3.68 (t, J=4.6 Hz, 1H), 3.46 (m, 2H), 3.01 (brs, 2H), 2.61~2.83 (m, 6H), 1.25~1.96 (m, 20H);

$^{13}$CNMR (75 MHz, CDCl$_3$): δ 161.5, 159.3, 154.4, 150.6, 148.0, 139.5, 137.5, 133.7, 128.2 (2C), 127.9 (2C), 127.5, 127.4, 127.2, 124.4, 124.0, 118.3, 115.6, 108.2, 67.4, 54.6, 49.6, 47.1, 34.1, 32.4, 31.8, 30.6, 29.5, 29.3, 28.2, 27.4, 26.9, 24.6, 23.0, 22.7, 18.9.

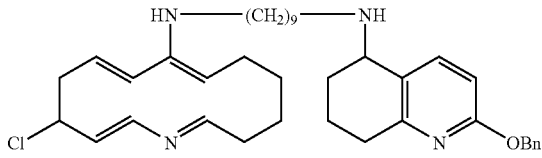

(S)-(2-Benzyloxy-5,6,7,8-tetrahydro-quinolin-5-yl)-N'-(6-chloro-1,2,3,4-tetrahydro-acridin-9-yl)-nonane-1,9-diamine (R)-(2-Benzyloxy-5,6,7,8-tetrahydro-quinolin-5-yl)-N'-(6-chloro-1,2,3,4-tetrahydro-acridin-9-yl)-nonane-1,9-diamine NMR (400 MHz, CDCl$_3$): δ 7.24~7.89 (m, 9H), 6.59 (d, J=8.3 Hz, 1H), 5.33 (s, 2H), 3.69 (m, 1H), 3.47 (t, J=7.1 Hz, 2H), 3.01 (brs, 2H), 2.61~2.82 (m, 6H), 1.25~1.96 (m, 22H);

$^{13}$CNMR (75 MHz, CDCl$_3$): δ 161.5, 159.3, 154.4, 150.6, 148.0, 139.5, 137.5, 133.7, 128.2 (2C), 127.9 (2C), 127.5, 127.4, 127.2, 124.5, 124.0, 118.3, 115.5, 108.2, 67.4, 54.6, 49.6, 47.1, 34.1, 32.4, 31.8, 30.6, 29.5 (2C), 29.3, 28.2, 27.4, 26.9, 24.6, 23.0, 22.7, 18.9.

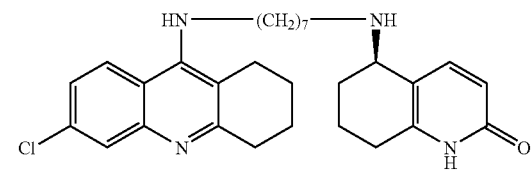

(6R)-5-[7-(6-Chloro-1,2,3,4-tetrahydro-acridin-9-ylamino)-heptylamino]-5,6,7,8-tetrahydro-1H-quinolin-2-one: To a solution of 30% hydrogen bromide in acetic acid (4 mL) cooled at 0° C., was added (R)—N-(2-benzyloxy-5,6,7, 8-tetrahydro-quinolin-5-yl)-N'-(6-chloro-1,2,3,4-tetrahydro-acridin-9-yl)-heptane-1,7-diamine (105 mg, 0.18 mmoL) in one portion. This mixture was stirred at 0° C. for 1 hour, and was allowed to warm up to room temperature. After 5 h, the reaction was quenched with 10% NaOH until pH value was up to 13. The mixture was then extracted with ethyl acetate (8 mL×3). The organic layers were combined, dried, filtered and concentrated. The resulting residue was purified by column chromatography using 2:3:0.5:0.5 (CH$_2$Cl$_2$/petroleum ether/MeOH/triethylamine) as eluent, to afford the desired product (33 mg, 0.0652 mmoL, 68% yield).

The following enantiomerically pure compounds were prepared according to the procedure described as above:
(6S)-5-[7-(6-Chloro-1,2,3,4-tetrahydro-acridin-9-ylamino)-heptylamino]-5,6,7,8-tetrahydro-1H-quinolin-2-one;
(6R)-5-[8-(6-Chloro-1,2,3,4-tetrahydro-acridin-9-ylamino)-octylamino]-5,6,7,8-tetrahydro-1H-quinolin-2-one;
(6S)-5-[8-(6-Chloro-1,2,3,4-tetrahydro-acridin-9-ylamino)-octylamino]-5,6,7,8-tetrahydro-1H-quinolin-2-one;
(6R)-5-[9-(6-Chloro-1,2,3,4-tetrahydro-acridin-9-ylamino)-nonylamino]-5,6,7,8-tetrahydro-1H-quinolin-2-one; and
(6S)-5-[9-(6-Chloro-1,2,3,4-tetrahydro-acridin-9-ylamino)-nonylamino]-5,6,7,8-tetrahydro-1H-quinolin-2-one.

What we claim is:

1. A compound of Formula I comprising a tetrahydroquinolinone moiety having an amino connecting substituent:

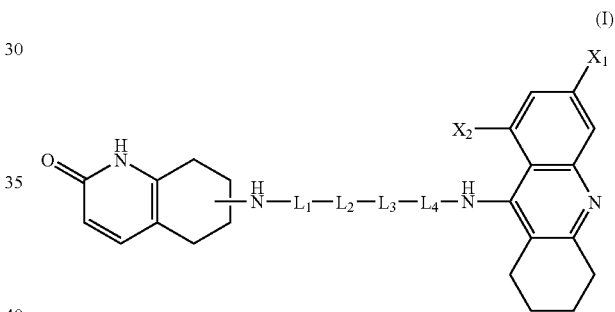

(I)

wherein
X$_1$, X$_2$ are independently selected from H, alkyl, halo, alkoxy;
L$_1$, L$_2$, L$_3$, L$_4$ are bonds independently selected from bivalent C$_{1-5}$ alkylene; 1,4-cyclohexylene, 1,4-phenylene, —CO—, —O—, —S— and —NR—;
R is selected from hydrogen, an unsubstituted or substituted alkyl, an unsubstituted or substituted cycloalkyl, unsubstituted or substituted alkenyl, or unsubstituted or substituted aryl; and
the amino connecting substituent is in either the 5 or 6 position of the tetrahydroquinolinone moiety;
with the proviso that if the amino connecting substituent of the tetrahydroquinolinone moiety is in the 5 position, and L$_1$-L$_2$-L$_3$-L$_4$ is a C$_{3-12}$ methylene linker, then one of X$_1$ or X$_2$ is not H.

2. A compound according to claim 1 wherein X$_1$ or X$_2$ is Cl.

3. A stereoisomer of a compound according to claim 1.

4. A pharmaceutical composition comprising a compound according to claim 1 in combination with a pharmaceutically acceptable excipient.

* * * * *